US 6,455,509 B1

(12) United States Patent
Kochel et al.

(10) Patent No.: US 6,455,509 B1
(45) Date of Patent: Sep. 24, 2002

(54) DENGUE NUCLEIC ACID VACCINES THAT INDUCE NEUTRALIZING ANTIBODIES

(75) Inventors: Tadeusz J. Kochel, Frederick; Kevin R. Porter, Gaithersburg; Kanakatte Raviprakash, Silver Spring; Stephen L. Hoffman, Gaithersburg; Curtis G. Hayes, Frederick, all of MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 08/869,423

(22) Filed: Jun. 4, 1997

Related U.S. Application Data

(60) Provisional application No. 60/017,839, filed on Jun. 4, 1996.

(51) Int. Cl.[7] ........................ A61K 31/711; A61K 39/12
(52) U.S. Cl. ........................ 514/44; 424/218.1
(58) Field of Search ............................ 424/184.1, 186.1, 424/202.1, 218.1; 514/44; 536/23.72

(56) References Cited

U.S. PATENT DOCUMENTS 5,494,671 A * 2/1996 Lai et al. .................. 424/218.1

FOREIGN PATENT DOCUMENTS

| FR | 2741077 | * | 5/1997 | |
| WO | 97/18311 | * | 5/1997 | ........... C12N/15/40 |

OTHER PUBLICATIONS

Phillpotts, R.J. et al. Arch. Virol. 141: 743–749, 1996.*
Bray, M. et al. Virology. 185 (1): 505–508, 1991.*
Kochel; Inoculation of Plasmids Expressing The Dengue–2 Envelope Gene Elicit Neutralizing Antibodies in Mice; Vaccine vol. 5. pp 547–552 1997.

Cox; Bovine Herpesvirus 1: Immune Responses in Mice And Cattle Injected with Plasmid DNA; Journal of Virology Sep. 1993; vol. 97, pp. 5664–5667.

Sedegah; Protection Against Malaria by Immunization with Plasmid DNA Encoding Circumsporozoite Protein; Proc. Natl, Acad. Sci,.; Oct. 1994; vol 91, pp. 9866–9870.

Major; DNA Based Immunization with Chimeric Vectors for the Induction of Immune Responses Against the Hepatitis C Virus Mucleocapsid; Journal of Virology; Sep. 1995; pp. 5798–5805.

Wang; Gene Inoculation Generates Immune Responses Against Human Immunodeficiency Virus Type 1; Proc. Natl. Acad. Sci.; May 1993; vol. 90, pp. 4156–4160.

Wolff; Direct Gene Transfer into Mouse Muscle in Vivo; Science vol.; Mar. 23, 1990; 1465–1468.

* cited by examiner

Primary Examiner—Mary E. Mosher
(74) Attorney, Agent, or Firm—Joseph K. Hemby, Jr.; Philip E. Ketner; Charles H. Harris

(57) ABSTRACT

A vaccine for promoting an immune response in a mammalian subject includes a eucaryotic plasmid expression vector which include at least part of the envelope gene and optionally, the PreM gene of dengue virus. In order to minimize immune enhancement, vaccines of up to the four serotypes of dengue are combined in a single vaccine. The vaccine in a suitable pharmaceutical carrier constitutes a pharmaceutical composition which is injected into the subject.

28 Claims, 4 Drawing Sheets

```
                        SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
           (A) LENGTH: 2357 base pairs
           (B) TYPE: nucleic acid
           (C) STRANDEDNESS: single
           (D) TOPOLOGY: linear (ii) MOLECULE TYPE: RNA (genomic)

(iii) HYPOTHETICAL: NO (iv) ANTI-SENSE: NO (v) FRAGMENT TYPE: internal (vi) ORIGINAL SOURCE:
           (A) ORGANISM: Dengue virus
           (B) STRAIN: New Guinea C (viii) POSITION IN GENOME:
           (A) CHROMOSOME/SEGMENT: PreM and Envelope
           (B) MAP POSITION: 330-2446
           (C) UNITS: bp (x) PUBLICATION INFORMATION:
           (A) AUTHORS: Gruenberg, A
               Woo, W S
               Biedrzycka, A
               Wright, P J
           (B) TITLE: Partial nucleotide sequence and deduced amino
               acid sequence of the structural proteins of dengue
               virus type 2, New Guinea C and PUO-218 strains
           (C) JOURNAL: J. Gen. Virol.
           (D) VOLUME: 69
           (F) PAGES: 1391-1398
           (G) DATE: 1988

(x) PUBLICATION INFORMATION:
           (A) AUTHORS: Irie, K
               Mohan, P M
               Sasaguri, Y
               Putnak, R
               Padmanabhan, R
```

(B) TITLE: Sequence Analysis of Cloned dengue virus type
2 genome (New Guinea-C strain)
(C) JOURNAL: Gene
(D) VOLUME: 75
(E) ISSUE: 2
(F) PAGES: 197-211
(G) DATE: 1989

(x) PUBLICATION INFORMATION:
(A) AUTHORS: Yaegashi, T
Vakharia, V N
Page, K
Sasaguri, Y
Feighny, R
Padmanabhan, R
(C) JOURNAL: Gene
(D) VOLUME: 46
(E) ISSUE: 2-3
(F) PAGES: 257-267
(G) DATE: 1986

(xi) SEQUENCE DESCRIPTION: SEQ ID NO:1:

```
AATTAGAGAG CAGATCTCTG ATGAATAACC AACGAAAAAA GGCGAGAAAT ACGCCTTTCA      60
ATATGCTGAA ACGCGAGAGA AACCGCGTGT CGACTGTACA ACAGCTGACA AAGAGATTCT     120
CACTTGGAAT GCTGCAGGGA CGAGGACCAT TAAAACTGTT CATGGCCCTG GTGGCGTTCC     180
TTCGTTTCCT AACAATCCCA CCAACAGCAG GGATACTGAA GAGATGGGGA ACAATTAAAA     240
AATCAAAAGC CATTAATGTT TTGAGAGGGT TCAGGAAAGA GATTGGAAGG ATGCTGAACA     300
TCTTGAACAG GAGACGCAGA ACTGCAGGCA TGATCATTAT GCTGATTCCA ACAGTGATGG     360
CGTTCCATTT AACCACACGT AACGGAGAAC CACACATGAT CGTCAGTAGA CAAGAGAAAG     420
GGAAAAGTCT TCTGTTTAAA ACAGAGGATG GTGTGAACAT GTGTACCCTC ATGGCCATGG     480
ACCTTGGTGA ATTGTGTGAA GATACAATCA CGTACAAGTG TCCTTTTCTC AGGCAGAATG     540
AACCAGAAGA CATAGATTGT TGGTGCAACT CTACGTCCAC ATGGGTAACT TATGGGACGT     600
GTACCACCAC AGGAGAACAC AGAAGAGAAA AAAGATCAGT GGCACTCGTT CCACATGTGG     660
GAATGGGACT GGAGACACGA ACTGAAACAT GGATGTCATC AGAAGGGGCC TGGAAACATG     720
CCCAGAGAAT TGAAACTTGG ATCTTGAGAC ATCCAGGCTT TACCATAATG GCAGCAATCC     780
TGGCATACAC CATAGGAACG ACACATTTCC AAAGAGCCCT GATTTTCATC TTACTGACAG     840
CTGTCGCTCC TTCAATGACA ATGCGTTGCA TAGGAATATC AAATAGAGAC TTTGTAGAAG     900
GGGTTTCAGG AGGAAGCTGG GTTGACATAG TCTTAGAACA TGGAAGCTGT GTGACGACGA     960
TGGCAAAAAA CAAACCAACA TTGGATTTTG AACTGATAAA AACAGAAGCC AAACAACCTG    1020
CCACTCTAAG GAAGTACTGT ATAGAGGCAA AGCTGACCAA CACAACAACA GATTCTCGCT    1080
GCCCAACACA AGGAGAACCC AGCCTAAATG AAGAGCAGGA CAAAAGGTTC GTCTGCAAAC    1140
ACTCCATGGT GGACAGAGGA TGGGGAAATG GATGTGGATT ATTTGGAAAA GGAGGCATTG    1200
TGACCTGTGC TATGTTCACA TGCAAAAAGA ACATGAAAGG AAAAGTCGTG CAACCAGAAA    1260
ACTTGGAATA CACCATTGTG ATAACACCTC ACTCAGGGGA AGAGCATGCA GTCGGAAATG    1320
ACACAGGAAA ACATGGCAAG GAAATCAAAA TAACACCACA GAGTTCCATC ACAGAAGCAG    1380
AGTTGACAGG CTATGGCACT GTCACGATGG AGTGCTCTCC GAGAACGGGC CTCGACTTCA    1440
ATGAGATGGT GTTGCTGCAA ATGGAAAATA AAGCTTGGCT GGTGCACAGG CAATGGTTCC    1500
TAGACCTGCC GTTGCCATGG CTGCCCGGAG CGGACACACA AGGATCAAAT TGGATACAGA    1560
AAGAGACATT GGTGACTTTC AAAAATCCCC ATGCGAAGAA ACAGGATGTT GTTGTTTTGG    1620
GATCCCAAGA AGGGGCCATG CACACAGCAC TCACAGGGGC CACAGAAATC CAGATGTCAT    1680
```

```
CAGGAAACTT ACTGTTCACA GGACATCTCA AGTGCAGGCT GAGGATGGAC AAACTACAGC    1740

TCAAAGGAAT GTCATACTCT ATGTGCACAG GAAAGTTTAA AGTTGTGAAG GAAATAGCAG    1800

AAACACAACA TGGAACAATA GTTATCAGAG TACAATATGA AGGGGACGGT TCTCCATGTA    1860

AGATCCCTTT TGAGATAATG GATTTGGAAA AAAGACATGT TTTAGGTCGC CTGATTACAG    1920

TCAACCCAAT CGTAACAGAA AAAGATAGCC CAGTCAACAT AGAAGCAGAA CCTCCATTCG    1980

GAGACAGCTA CATCATCATA GGAGTAGAGC CGGGACAATT GAAGCTCAAC TGGTTTAAGA    2040

AAGGAAGTTC TATCGGCCAA ATGATTGAGA CAACAATGAG GGGAGCGAAG AGAATGGCCA    2100

TTTTAGGTGA CACAGCTTGG GATTTTGGAT CCCTGGGAGG AGTGTTTACA TCTATAGGAA    2160

AGGCTCTCCA CCAAGTTTTC GGAGCAATCT ATGGGGCTGC CTTCAGTGGG GTCTCATGGA    2220

CTATGAAAAT CCTCATAGGA GTCATTATCA CATGGATAGG AATGAATTCA CGCAGCACCT    2280

CACTTTCTGT GTCACTAGTA TTGGTGGGAG TCGTGACGCT GTATTTGGGA GTTATGGTGC    2340

AGGCCGATAG TGGTTGC                                                  2357

(2) INFORMATION FOR SEQ ID NO:2:

(i) SEQUENCE CHARACTERISTICS:
        (A) LENGTH: 1941 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 34..531
        (C) IDENTIFICATION METHOD: experimental
        (D) OTHER INFORMATION: /product= "preM"
            /evidence= EXPERIMENTAL
            /standard_name= "Membrane protein"

(ix) FEATURE:
        (A) NAME/KEY: misc_feature
        (B) LOCATION: 532..1920
        (C) IDENTIFICATION METHOD: experimental
        (D) OTHER INFORMATION: /product= "E"
            /evidence= EXPERIMENTAL
            /standard_name= "Envelope protein"

(ix) FEATURE:
        (A) NAME/KEY: misc_feature
        (B) LOCATION: 1921..1938
        (C) IDENTIFICATION METHOD: experimental
        (D) OTHER INFORMATION: /product= "Additional amino acids"
            /evidence= EXPERIMENTAL (ix) FEATURE:
        (A) NAME/KEY: misc_signal
        (B) LOCATION: 1..33
        (C) IDENTIFICATION METHOD: experimental
        (D) OTHER INFORMATION: /function= "Signal sequence"
            /evidence= EXPERIMENTAL (xi) SEQUENCE DESCRIPTION: SEQ ID NO:2:

ATGATCATTA TGCTGATTCC AACAGTGATG GCGTTCCATT TAACCACACG TAACGGAGAA      60

CCACACATGA TCGTCAGTAG ACAAGAGAAA GGGAAAAGTC TTCTGTTTAA AACAGAGGAT     120

GGTGTGAACA TGTGTACCCT CATGGCCATG GACCTTGGTG AATTGTGTGA AGATACAATC     180

ACGTACAAGT GTCCTTTTCT CAAGCAGAAT GAACCAGAAG ACATAGATTG TTGGTGCAAC     240

TCTACGTCCA CATGGGTAAC TTATGGGACG TGTACCACCA CAGGAGAACA CAGAAGAGAA     300

AAAAGATCAG TGGCACTCGT TCCACATGTG GGAATGGGAC TGGAGACACG AACTGAAACA     360

TGGATGTCAT CAGAAGGGGC CTGGAAACAT GCCCAGAGAA TTGAAACTTG GATCTTGAGA     420
```

```
CATCCAGGCT TTACCATAAT GGCAGCAATC CTGGCATACA CCATAGGAAC GACACATTTC    480

CAAAGAGCCC TGATTTTCAT CTTACTGACA GCTGTCGCTC CTTCAATGAC AATGCGTTGC    540

ATAGGAATAT CAAATAGAGA CTTTGTAGAA GGGGTTTCAG GAGGAAGCTG GGTTGACATA    600

GTCTTAGAAC ATGGAAGCTG TGTGACGACG ATGGCAAAAA ACAAACCAAC ATTGGATTTT    660

GAACTGATAA AAACAGAAGC CAAACAACCT GCCACTCTAA GGAAGTACTG TATAGAGGCA    720

AAGCTGACCA ACACAACAAC AGATTCTCGC TGCCCAACAC AAGGAGAACC CAGCCTAAAT    780

GAAGAGCAGG ACAAAAGGTT CGTCTGCAAA CACTCCATGG TGGACAGAGG ATGGGGAAAT    840

GGATGTGGAT TATTTGGAAA AGGAGGCATT GTGACCTGTG CTATGTTCAC ATGCAAAAAG    900

AACATGAAAG GAAAAGTCGT GCAACCAGAA AACTTGGAAT ACACCATTGT GATAACACCT    960

CACTCAGGGG AAGAGCATGC AGTCGGAAAT GACACAGGAA ACATGGCAA GGAAATCAAA   1020

ATAACACCAC AGAGTTCCAT CACAGAAGCA GAGTTGACAG GCTATGGCAC TGTCACGATG   1080

GAGTGCTCTC CGAGAACGGG CCTCGACTTC AATGAGATGG TGTTGCTGCA AATGGAAAAT   1140

AAAGCTTGGC TGGTGCACAG GCAATGGTTC CTAGACCTGC CGTTGCCATG GCTGCCCGGA   1200

GCGGACACAC AAGGATCAAA TTGGATACAG AAAGAGACAT TGGTGACTTT CAAAAATCCC   1260

CATGCGAAGA AACAGGATGT TGTTGTTTTG GGATCCCAAG AAGGGGCCAT GCACACAGCA   1320

CTCACAGGGG CCACAGAAAT CCAGATGTCA TCAGGAAACT TACTGTTCAC AGGACATCTC   1380

AAGTGCAGGC TGAGGATGGA CAAACTACAG CTCAAAGGAA TGTCATACTC TATGTGCACA   1440

GGAAAGTTTA AAGTTGTGAA GGAAATAGCA GAAACACAAC ATGGAACAAT AGTTATCAGA   1500

GTACAATATG AAGGGGACGG TTCTCCATGT AAGATCCCTT TTGAGATAAT GGATTTGGAA   1560

AAAAGACATG TTTTAGGTCG CCTGATTACA GTCAACCCAA TCGTAACAGA AAAAGATAGC   1620

CCAGTCAACA TAGAAGCAGA ACCTCCATTC GGAGACAGCT ACATCATCAT AGGAGTAGAG   1680

CCGGGACAAT TGAAGCTCAA CTGGTTTAAG AAAGGAAGTT CTATCGGCCA AATGATTGAG   1740

ACAACAATGA GGGGAGCGAA GAGAATGGCC ATTTTAGGTG ACACAGCTTG GGATTTTGGA   1800

TCCCTGGGAG GAGTGTTTAC ATCTATAGGA AAGGCTCTCC ACCAAGTTTT CGGAGCAATC   1860

TATGGGGCTG CCTTCAGTGG GGTCTCATGG AATATGAAAA TCCTCATAGG AGTCATTATG   1920

GAATTATCGC GGCCGCTCTA G                                             1941
```

(2) INFORMATION FOR SEQ ID NO:3:

(i) SEQUENCE CHARACTERISTICS:
        (A) LENGTH: 2016 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 34..531
        (C) IDENTIFICATION METHOD: experimental
        (D) OTHER INFORMATION: /product= "PreM"
            /evidence= EXPERIMENTAL
            /standard_name= "Membrane protein"

(ix) FEATURE:
        (A) NAME/KEY: misc_feature
        (B) LOCATION: 532..2016
        (C) IDENTIFICATION METHOD: experimental
        (D) OTHER INFORMATION: /product= "E"
            /evidence= EXPERIMENTAL
            /standard_name= "Envelope"

(ix) FEATURE:
        (A) NAME/KEY: misc_signal (B) LOCATION: 1..33
(C) IDENTIFICATION METHOD: experimental
(D) OTHER INFORMATION: /function= "Signal sequence"
    /evidence= EXPERIMENTAL (xi) SEQUENCE DESCRIPTION: SEQ ID NO:3:

| | | | | | |
|---|---|---|---|---|---|
| ATGATCATTA | TGCTGATTCC | AACAGTGATG | GCGTTCCATT | TAACCACACG | TAACGGAGAA | 60 |
| CCACACATGA | TCGTCAGTAG | ACAAGAGAAA | GGGAAAAGTC | TTCTGTTTAA | AACAAAGGAT | 120 |
| GGTGTGAACA | TGTGTACCCT | CATGGCCATG | GACCTTGGTG | AATTGTGTGA | AGATACAATC | 180 |
| ACGTACAAGT | GTCCTCTTCT | CAAGCAGAAT | GAACCAGAAG | ACATAGATTG | TTGGTGCAAC | 240 |
| TCTACGTCCA | CATGGGCAAC | TTATGGGACG | TGTACCACCA | CAGGAGAACA | CAGAAGAGAA | 300 |
| AAAAGATCAG | TGGCACTCGT | TCCACATGTG | GGAATGGGAC | TGGAGACACG | AACTGAAACA | 360 |
| TGGATGTCAT | CAGAAGGGGC | CTGGAAACAT | GCCCAGAGAA | TTGAAACTTG | GATCTTGAGA | 420 |
| CATCCAGGCT | TTACCATAAT | GGCAGCAATC | CTGGCATACA | CCATAGGAAC | GACACATTTC | 480 |
| CAAAGAGCCC | TGATTTTCAT | CTTACTGACA | GCTGTCGCTC | CTTCAATGAC | AATGCGTTGC | 540 |
| ATAGGAATAT | CAAATAGAGA | CTTTGTAGAA | GGGGTTTCAG | GAGGAAGCTG | GGTTGACATA | 600 |
| GTCTTAGAAC | ATGGAAGCTG | TGTGACGACG | ATGGCAAAAA | ACAAACCAAC | ATTGGATTTT | 660 |
| GAACTGATAA | AAACAGAAGC | CAAACAACCT | GCCACTCTAA | GGAAGTACTG | TATAGAGGCA | 720 |
| AAGCTGACCA | ACACAACAAC | AGAATCTCGC | TGCCCAACAC | AAGGAGAACC | CAGCCTAAAT | 780 |
| GAAGAGCAGG | ACAAAAGGTT | CGTCTGCAAA | CACTCCATGG | TGGACAGAGG | ATGGGGAAAT | 840 |
| GGATGTGGAC | TATTTGGAAA | AGGAGGCATT | GTGACCTGTG | CTATGTTCAA | ATGCAAAAAG | 900 |
| AACATGGAAG | GAAAAGTCGT | GCAACCAGAA | AACTTGGAAT | ACACCATTGT | GATAACACCT | 960 |
| CACTCAGGGG | AAGAGCATGC | AGTCGGAAAT | GACACAGGAA | ACATGGCAA | GGAAATCAAA | 1020 |
| ATAACACCAC | AGAGTTCCAT | CACAGAAGCA | GAGTTGACAG | GCTATGGCAC | TGTCACGATG | 1080 |
| GAGTGCTCTC | CGAGAACGGG | CCTCGACTTC | AATGAGATGG | TGTTGCTGCA | AATGGAAAAT | 1140 |
| AAAGCTTGGC | TGGTGCACAG | GCAATGGTTC | CTAGACCTGC | CGTTGCCATG | GCTGCCCGGA | 1200 |
| GCGGACACAC | AAGGATCAAA | TTGGATACAG | AAAGAGACAT | TGGTCACTTT | CAAAAATCCC | 1260 |
| CATGCGAAGA | AACAGGATGT | TGTTGTTTTG | GGATCCCAAG | AAGGGGCCAT | GCACACAGCA | 1320 |
| CTCACAGGGG | CCACAGAAAT | CCAGATGTCA | TCAGGAAACT | TACTGTTCAC | AGGACATCTC | 1380 |
| AAGTGCAGGC | TGAGGATGGA | CAAACTACAG | CTCAAAGGAA | TGTCATACTC | TATGTGCACA | 1440 |
| GGAAAGTTTA | AAGTTGTGAA | GGAAATAGCA | GAAACACAAC | ATGGAACAAT | AGTTATCAGA | 1500 |
| GTACAATATG | AAGGGGACGG | TTCTCCATGT | AAGATCCCTT | TTGAGATAAT | GGATTTGGAA | 1560 |
| AAAAGACATG | TTTTAGGTCG | CCTGATTACA | GTCAACCCAA | TCGTAACAGA | AAAAGATAGC | 1620 |
| CCAGTCAACA | TAGAAGCAGA | ACCTCCATTC | GGAGACAGCC | ACATCATCAT | AGGAGTAGAG | 1680 |
| CCGGGACAAT | TGAAGCTCAA | CTGGTTTAAG | AAAGGAAGTT | CTATCGGCCA | AATGTTTGAG | 1740 |
| ACAACAATGA | GGGGAGCGAA | GAGAATGGCC | ATTTTAGGTG | ACACAGCTTG | GGATTTTGGA | 1800 |
| TCCCTGGGAG | GAGTGTTTAC | ATCTATAGGA | AAGGCTCTCC | ACCAAGTTTT | CGGAGCAATC | 1860 |
| TATGGGGCTG | CCTTCAGTGG | GGTCTCATGG | ACTATGAAAA | TCCTCATAGG | AGTCATTATC | 1920 |
| ACATGGATAG | GAATGAATTC | ACGCAGCACC | TCACTGTCTG | TGTCACTAGT | ATTGGTGGGA | 1980 |
| GTCGTGACGC | TGTATTTGGG | AGTTATGGTG | CAGGCC | | | 2016 |

(2) INFORMATION FOR SEQ ID NO:4:

(i) SEQUENCE CHARACTERISTICS:

(A) LENGTH: 2042 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..59
        (C) IDENTIFICATION METHOD: experimental
        (D) OTHER INFORMATION: /product= "PreM Signal Sequence"
            /evidence= EXPERIMENTAL (ix) FEATURE:
        (A) NAME/KEY: misc_feature
        (B) LOCATION: 60..497
        (C) IDENTIFICATION METHOD: experimental
        (D) OTHER INFORMATION: /product= "PreM"
            /evidence= EXPERIMENTAL (ix) FEATURE:
        (A) NAME/KEY: misc_feature
        (B) LOCATION: 498..2042
        (C) IDENTIFICATION METHOD: experimental
        (D) OTHER INFORMATION: /product= "Envelope"
            /evidence= EXPERIMENTAL (x) PUBLICATION INFORMATION:
        (A) AUTHORS: Mason, P W
            McAda, P C
            Mason, T L
            Fournier, M J
        (B) TITLE: Sequence of the dengue-1 virus genome in the
            region encoding the three structural proteins and
            the major nonstructural protein NS1
        (C) JOURNAL: Virology
        (D) VOLUME: 161
        (F) PAGES: 252-267
        (K) RELEVANT RESIDUES IN SEQ ID NO:4: FROM 1 TO 2400

(x) PUBLICATION INFORMATION:
        (A) AUTHORS: Fu, J
            Tan, B H
            Yap, E H
            Chan, Y C
            Tan, Y H
        (B) TITLE: Full-length cDNA sequence of dengue type-1
            virus (Singapore strain S275/90)
        (C) JOURNAL: Virology
        (D) VOLUME: 188
        (E) ISSUE: 2
        (F) PAGES: 953-958
        (G) DATE: 1992
        (K) RELEVANT RESIDUES IN SEQ ID NO:4: FROM 1 TO 10984

(xi) SEQUENCE DESCRIPTION: SEQ ID NO:4:

ATGAACAGGA GGAAAAGATC TGTGACCATG CTCCTCATGC TGCTGCCCAC AGCCCTGGCG      60

TTCCATCTGA CCACCCGAGG GGGAGAGCCG CACATGATAG TTAGCAAGCA GGAAAGAGGA     120

AAATCACTTT TGTTTAAGAC TCTCTGCAGGT GTCAACATGT GCACCCTTAT TGCAATGGAT     180

TTGGGAGAGT TATGTGAGGA CACAATGACC TACAAATGCC CCCGGATCAC TGAGACGGAA     240

CCAGATGACG TTGACTGTTG GTGCAATGCC ACGGAGACAT GGGTGACCTA TGGAACATGT     300

TCTCAAACTG GTGAACACCG ACGAGACAAA CGTTCCGTCG CACTGGCACC ACACGTAGGG     360

CTTGGTCTAG AAACAAGAAC CGAAACGTGG ATGTCCTCTG AAGGCGCTTG GAAACAAATA     420

CAAAAAGTGG AGACCTGGGC TCTGAGACAC CCAGGATTCA CGGTGATAGC CCTTTTTCTA     480

GCACATGCCA TAGGAACATC CATCACCCAG AAAGGGATAT TTTTATTTTG CTGATGCTGG     540

TAACTCCATC CATGGCCATG CGGTGCGTGG GAATAGGCAA CAGAGACTTC GTGGAAGGAC     600

TGTCAGGAGC TACGTGGGTG GATGTGGTAC TGGAGCATGG AAGTTGCGTC ACTACCATGG     660

CAAAAGACAA ACCAACACTG GACATTGAAC TCTTGAAGAC GGAGGTCACA AACCCTGCCG     720

```
TCCTGCGCAA ACTGTGCATT GAAGCTAAAA TATCAAACAC CACCACCGAT TCGAGATGTC    780

CAACACAAGG AGAAGCCACG CTGGTGGAAG AACAGGACAC GAACTTTGTG TGTCGACGAA    840

CGTTCGTGGA CAGAGGCTGG GGCAATGGTT GTGGGCTATT CGGAAAAGGT AGCTTAATAA    900

CGTGTGCTAA GTTTAAGTGT GTGACAAAAC TGGAAGGAAA GATAGTCCAA TATGAAAACT    960

TAAAATATTC AGTGATAGTC ACCGTACACA CTGGAGACCA GCACCAAGTT GGAAATGAGA   1020

CCACAGAACA TGGAACAACT GCAACCATAA CACCTCAAGC TCCCACGTCG GAAATACAGC   1080

TGACAGACTA CGGAGCTCTA ACATTGGATT GTTCACCTAG AACAGGGCTA GACTTTAATG   1140

AGATGGTGTT GTTGACAATG GAAAAAAAAT CATGGCTCGT CCACAAACAA TGGTTTCTAG   1200

ACTTACCACT GCCTTGGACC TCGGGGGCTT CAACATCCCA AGAGACTTGG AATAGACAAG   1260

ACTTGCTGGT CACATTTAAG ACAGCTCATG CAAAAAAGCA GGAAGTAGTC GTACTAGGAT   1320

CACAAGAAGG AGCAATGCAC ACTGCGTTGA CTGGAGCGAC AGAAATCCAA ACGTCTGGAA   1380

CGACAACAAT TTTTGCAGGA CACCTGAAAT GCAGACTAAA AATGGATAAA CTGACTTTAA   1440

AAGGGATGTC ATATGTAATG TGCACAGGGT CATTCAAGTT AGAGAAGGAA GTGGCTGAGA   1500

CCCAGCATGG AACTGTTCTA GTGCAGGTTA AATACGAAGG AACAGATGCA CCATGCAAGA   1560

TCCCCTTCTC GTCCCAAGAT GAGAAGGGAG TAACCCAGAA TGGAGATTG ATAACAGCCA   1620

ACCCCATAGT CACTGACAAA GAAAAACCAG TCAACATTGA AGCGGAGCCA CCTTTTGGTG   1680

AGAGCTACAT TGTGGTAGGA GCAGGTGAAA AAGCTTTGAA ACTAAGCTGG TTCAAGAAGG   1740

GAAGCAGTAT AGGGAAAATG TTTGAAGCAA CTGCCCGTGG AGCACGAAGG ATGGCCATCC   1800

TGGGAGACAC TGCATGGGAC TTCGGTTCTA TAGGAGGGGT GTTCACGTCT GTGGGAAAAC   1860

TGATACACCA GATTTTTGGG ACTGCGTATG GAGTTTTGTT CAGCGGTGTT TCTTGGACCA   1920

TGAAGATAGG AATAGGGATT CTGCTGACAT GGCTAGGATT AAACTCAAGG AGCACGTCCC   1980

TTTCAATGAC GTGTATCGCA GTTGGCATGG TCACGCTGTA CCTAGGAGTC ATGGTTCAGG   2040

CG                                                                 2042

(2) INFORMATION FOR SEQ ID NO:5:

(i) SEQUENCE CHARACTERISTICS:
        (A) LENGTH: 2049 base pairs
        (B) TYPE: nucleic acid
        (C) STRANDEDNESS: single
        (D) TOPOLOGY: linear (ix) FEATURE:
        (A) NAME/KEY: misc_signal
        (B) LOCATION: 1..71
        (D) OTHER INFORMATION: /function= "Signal Sequence"

(ix) FEATURE:
        (A) NAME/KEY: misc_feature
        (B) LOCATION: 72..497
        (C) IDENTIFICATION METHOD: experimental
        (D) OTHER INFORMATION: /product= "PreM"
            /evidence= EXPERIMENTAL
            /standard_name= "Membrane protein"

(ix) FEATURE:
        (A) NAME/KEY: misc_feature
        (B) LOCATION: 498..2049
        (C) IDENTIFICATION METHOD: experimental
        (D) OTHER INFORMATION: /product= "E"
            /evidence= EXPERIMENTAL
            /standard_name= "Envelope protein"

(x) PUBLICATION INFORMATION:
        (A) AUTHORS: Osatomi, K
```

Fuke, I
Tsuru, D
Shiba, T
Sakaki, Y
Sumiyoshi, H
   (B) TITLE: Nucleotide sequence of dengue type 3 virus
       genomic RNA encoding viral structural proteins
   (C) JOURNAL: Virus Genes
   (D) VOLUME: 2
   (E) ISSUE: 1
   (F) PAGES: 99-108
   (G) DATE: 1988

(x) PUBLICATION INFORMATION:
   (A) AUTHORS: Osatomi, K
       Sumiyoshi, H
   (B) TITLE: Complete nucleotide sequence of dengue 3
       virus genome RNA
   (C) JOURNAL: Virology
   (D) VOLUME: 176
   (E) ISSUE: 2
   (F) PAGES: 643-647
   (G) DATE: 1990

(xi) SEQUENCE DESCRIPTION: SEQ ID NO:5:

```
ATGCTGAGCA TTATCAACAA ACGGAAAAAG ACATCGCTCT GTCTCATGAT GATGTTACCA      60
GCAACACTTG CTTTCCACTT AACTTCACGA GATGGAGAGC CGCGCATGAT TGTGGGGAAG     120
AATGAAAGAG GAAAATCCCT ACTTTTTAAG ACAGCCTCTG GAATCAACAT GTGCACACTC     180
ATAGCCATGG ATTTGGGAGA GATGTGTGAT GACACGGTCA CTTACAAATG CCCCCACATT     240
ACCGAAGTGG AGCCTGAAGA CATTGACTGT TGGTGCAACC TTACATCGAC ATGGGTGACT     300
TATGGAACAT GCAATCAAGC TGGAGAGCAT AGACGCGATA AGAGATCAGT GGCGTTAGCT     360
CCCCATGTCG GCATGGGACT GGACACACGC ACTCAAACCT GGATGTCGGC TGAAGGAGCT     420
TGGAGACAAG TCGAGAAGGT AGAGACATGG GCCCTTAGGC ACCCAGGGTT TACCATACTA     480
GCCCTATTTC TTGCCCATTA CATAGGCACT TCCTTGACCC AGAAAGTGGT TATTTTTATA     540
CTATTAATGC TGGTTACCCC ATCCATGACA ATGAGATGTG TGGGAGTAGG AAACAGAGAT     600
TTTGTGGAAG GCCTATCGGG AGCTACGTGG GTTGACGTGG TGCTCGAGCA CGGTGGGTGT     660
GTGACTACCA TGGCTAAGAA CAAGCCCACG CTGGACATAG AGCTTCAGAA GACTGAGGCC     720
ACTCAGCTGG CGACCCTAAG GAAGCTATGC ATTGAGGGAA AAATTACCAA CATAACAACC     780
GACTCAAGAT GTCCCACCCA AGGGGAAGCG ATTTTACCTG AGGAGCAGGA CCAGAACTAC     840
GTGTGTAAGC ATACATACGT GGACAGAGGC TGGGGAAACG GTTGTGGTTT GTTTGGCAAG     900
GGAAGCTTGG TGACATGCGC GAAATTTCAA TGTTTAGAAT CAATAGAGGG AAAAGTGGTG     960
CAACATGAGA ACCTCAAATA CACCGTCATC ATCACAGTGC ACACAGGAGA CCAACACCAG    1020
GTGGGAAATG AAACGCAGGG AGTTACGGCT GAGATAACAT CCCAGGCATC AACCGCTGAA    1080
GCCATTTTAC CTGAATATGG AACCCTCGGG CTAGAATGCT CACCACGGAC AGGTTTGGAT    1140
TTCAATGAAA TGATTTTATT GACAATGAAG AACAAAGCAT GGATGGTACA TAGACAATGG    1200
TTCTTTGACT TACCCCTACC ATGGACATCA GGAGCTACAA CAAAAACACC AACTTGGAAC    1260
AGGAAAGAGC TTCTTGTGAC ATTTAAAAAT GCACATGCAA AAAGCAAGA AGTAGTTGTC    1320
CTTGGATCAC AAGAGGGAGC AATGCATACA GCACTGACAG GAGCTACAGA GATCCAAACC    1380
TCAGGAGGCA CAAGTATTTT TGCGGGGCAC TTAAAATGTA GACTCAAGAT GGACAAATTG    1440
AAACTCAAGG GGATGAGCTA TGCAATGTGC TTGAATACCT TTGTGTTGAA GAAAGAAGTC    1500
TCCGAAACGC AGCATGGGAC AATACTCATT AAGGTTGAGT ACAAAGGGGA AGATGCACCC    1560
TGCAAGATTC CTTTCTCCAC GGAGGATGGA CAAGGGAAAG CTCACAATGG CAGACTGATC    1620
```

-continued

```
ACAGCCAATC CAGTGGTGAC CAAGAAGGAG GAGCCTGTCA ACATTGAGGC TGAACCTCCT     1680

TTTGGGGAAA GTAATATAGT AATTGGAATT GGAGACAAAG CCCTGAAAAT CAACTGGTAC     1740

AGGAAGGGAA GCTCGATTGG GAAGATGTTC GAGGCCACTG CCAGAGGTGC AAGGCGCATG     1800

GCCATCTTGG GAGACACAGC CTGGGACTTT GGATCAGTGG GTGGTGTTTT GAATTCATTA     1860

GGGAAAATGG TCCACCAAAT ATTTGGGAGT GCTTACACAG CCCTATTTAG TGGAGTCTCC     1920

TGGATAATGA AAATTGGAAT AGGTGTCCTC TTAACCTGGA TAGGGTTGAA TTCAAAAAAC     1980

ACTTCTATGT CATTTTCATG CATTGCGATA GGAATCATTA CACTCTATCT GGGGGTCGTG     2040

GTGCAAGCT                                                             2049
```

(2) INFORMATION FOR SEQ ID NO:6:

(i) SEQUENCE CHARACTERISTICS:
        (A) LENGTH: 2052 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..72
        (C) IDENTIFICATION METHOD: experimental
        (D) OTHER INFORMATION: /product= "PreM Signal Sequence"
            /evidence= EXPERIMENTAL (ix) FEATURE:
        (A) NAME/KEY: misc_feature
        (B) LOCATION: 73..569
        (C) IDENTIFICATION METHOD: experimental
        (D) OTHER INFORMATION: /product= "PreM"
            /evidence= EXPERIMENTAL (ix) FEATURE:
        (A) NAME/KEY: misc_feature
        (B) LOCATION: 570..2052
        (D) OTHER INFORMATION: /product= "Envelope"

(x) PUBLICATION INFORMATION:
        (A) AUTHORS: Zhao, B
            Mackow, E
            Buckler,
            White, A
        (B) TITLE: Cloning full length dengue type-4 viral DNA
            sequences: analysis of genes coding for structural
            proteins
        (C) JOURNAL: Virology
        (D) VOLUME: 155
        (E) ISSUE: 1
        (F) PAGES: 77-88
        (G) DATE: 1986

(xi) SEQUENCE DESCRIPTION: SEQ ID NO:6:

```
ATGCTGAACA TCTTGAATGG GAGAAAAAGG TCAACAATGA CATTGCTGTG CTTGATTCCC       60

ACCGTAATGG CGTTTCACTT GTCAACAAGA GATGGCGAAC CCCTTATGAT AGTGGCAAAA      120

CACGAAAGGG GGAGACCTCT CTTGTTTAAG ACAACAGAGG GAATCAACAA ATGCACTCTT      180

ATTGCCATGG ACCTGGGTGA AATGTGTGAG ACACCGTCA CGTATGAGTG CCCTCTACTG       240

GTCAATACCG AACCTGAGGA CATTGATTGC TGGTGCAATC TCACGTCTGC GTGGGTCATG      300

TATGGGACAT GCACTCAGAG TGGGGAACGG AGACGGGAGA AGCGCTCAGT AGCCCTAACA      360

CCACATTCAG GAATGGGATT GGAGACAAGG GCTGAGACAT GGATGTCATC GGAAGGGGCT      420

TGGAAACATG CTCAGAGGGT AGAGAGTTGG ATACTCAGAA ACCCAGGATT CGCTCTCTTG      480

GCAGGATTTA TGGCCTATAT GATTGGGCAA ACAGGAATCC AGCGAACAGT CTTCTTTGTT      540
```

```
CTAATGATGC TGGTCGCCCC ATCCTACGGA ATGCGATGCG TGGGAGTGGG GAACAGAGAC    600

TTTGTGGAAG GAGTCTCAGG TGGAGCATGG GTCGATTCGG TGCTAGAACA TGGAGGATGT    660

GTCACAACCA TGGCCCAGGG AAAACCAACC TTGGATTTTG AACTGATCAA GACAACAGCC    720

AAGGAAGTGG CTCTGTTAAG AACCTATTGC ATTGAAGCCT CGATATCAAA CATAACCACG    780

GCAACAAGAT GTCCAACGCA AGGAGAACCT TATCTCAAAG AGGAACAAGA TCAACAGTAC    840

ATTTGCCGGA GAGATGTGGT AGACAGAGGG TGGGGCAATG GCTGTGGCTT GTTTGGGAAA    900

GGAGGAGTTG TGACATGTGC GAAGTTTTCA TGCTCGGGGA AGATAACAGG CAATTTGGTC    960

CAAATTGAGA ACCTTGAATA CACAGTGATT GTAACAGTCC ACAATGGAGA CACCCATGCA   1020

GTAGGAAATG ACACATCCAA CCATGGAGTG ACAGCCACGA TAACCCCCAG GTCACCATCG   1080

GTAGAAGTTA AATTACCGGA TTATGGAGAA TTAACACTCG ATTGTGAACC CAGGTCCGGA   1140

ATTGATTTTA ATGAGATGAT TCTGATGAAA ATGAAAAAGA AAACGTGGCT TGTGCACAAG   1200

CAATGGTTTT TGGATCTACC TCTACCATGG GCAGCAGGAG CAGACACATC AGAAGTTCAT   1260

TGGAATTACA AAGAGAGAAT GGTGACATTC AAGGTTCCTC ATGCCAAGAG ACAGGATGTG   1320

ATAGTGCTAG GATCTCAGGA AGGAGCCATG CATTCTGCCC TCACCGGAGC TACAGAAGTG   1380

GATTCCGGTG ATGGAAACCA CATGTTTGCA GGACATCTTA AATGCAAAGT TCGCATGGAG   1440

AAATTGAGAA TTAAGGGAAT GTCATACACG ATGTGCTCAG GAAAGTTCTC AATTGACAAA   1500

GAGATGGCAG AAACACAGCA TGGGACAACA GTGGTAAAAG TCAAGTATGA GGGTGCTGGA   1560

GCTCCATGTA AAGTTCCCAT AGAGATAAGA GATGTGAACA AGGAAAAAGT GGTAGGGCGT   1620

ATCATCTCAC CTACCCCTTT TGCTGAGAAT ACCAACAGTG TAACCAACAT AGAATTAGAA   1680

CGCCCTTTGG ACAGCTACAT AGTAATAGGT GTTGGAGACA GCGCATTAAC ACTCCATTGG   1740

TTCAGGAAAG GGAGTTCCAT TGGCAAGATG TTTGAGTCCA CATACAGAGG CGCAAAGCGA   1800

ATGGCCATTC TAGGTGAAAC AGCCTGGGAT TTTGGTTCTG TTGGTGGACT GCTCACATCA   1860

TTGGGAAAGG CTGTACACCA GGTTTTTGGT AGTGTGTATA CAACTATGTT TGGAGGAGTC   1920

TCATGGATGG TTAGAATCCT AATTGGGTTC TTAGTGTTGT GGATTGGCAC GAACTCGAGG   1980

AACACTTCAA TGGCTATGAC GTGCATAGCT GTTGGAGGAA TCACTCTGTT TCTGGGCTTC   2040

ACAGTTCAAG CA                                                      2052
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

```
CATTGGATTT TGAACTGA                                                  18
```

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

```
GTCACGATGG AGTGCTCT                                                  18
```

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

```
GGATGTTGTT GTTTTGGGAT                                              20
```

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:10:

```
CCTCTATACA GTACTTCCTT AGAGTGGC                                     28
```

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:11:

```
GGTAACTCCC GTTGCGGTTC TG                                           22
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

```
CATGGAAGCC ATCACAGACG GC                                           22
```

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:13:

```
ACGTCTCGAG AGGACCATGG CTGTGACCAT GCTCCTCATG CT                     42
```

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:14:

```
ACGTCTCGAG AGGACCATGG GGATCATTTT TATTTTGCTG AT                     42
```

(2) INFORMATION FOR SEQ ID NO:15:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (xi) SEQUENCE DESCRIPTION: SEQ ID NO:15:

ACGTGGATCC TCATTACTTC TTGAACCAGC TTAGTTTCA                          39

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:16:

AGTGGATCCT CATTACTTCA TGGTCCAAGA AACACC                             36

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:17:

AGTGGATCCT CATTACGCCT GAACCATGAC TCCTAG                             36

(2) INFORMATION FOR SEQ ID NO:18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:18:

TCCACACTTC AATTC                                                    15

(2) INFORMATION FOR SEQ ID NO:19:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:19:

ATACTGCAGG CATGCTGAAC ATCCTGAACG GGAGAAAAAG G                       41

(2) INFORMATION FOR SEQ ID NO:20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:20:

TATGATCCTT ATGCTTGAAC TGTGAAGCCC AGAAACAGAG TG                      42

(2) INFORMATION FOR SEQ ID NO:21:

```
        (i) SEQUENCE CHARACTERISTICS:
             (A) LENGTH: 17 base pairs
             (B) TYPE: nucleic acid
             (C) STRANDEDNESS: single
             (D) TOPOLOGY: linear (xi) SEQUENCE DESCRIPTION: SEQ ID NO:21:

GACTAAAGGT ACGGTAT                                                  17

(2) INFORMATION FOR SEQ ID NO:22:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (xi) SEQUENCE DESCRIPTION: SEQ ID NO:22:

GACTAAAGGT ACGGTAT                                                  17

(2) INFORMATION FOR SEQ ID NO:23:

(i) SEQUENCE CHARACTERISTICS:
             (A) LENGTH: 38 base pairs
             (B) TYPE: nucleic acid
             (C) STRANDEDNESS: single
             (D) TOPOLOGY: linear (xi) SEQUENCE DESCRIPTION: SEQ ID NO:23:

AAACTGCAGC CATGCTGAGC ATTATCAACA AACGGAAA                            38

(2) INFORMATION FOR SEQ ID NO:24:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (xi) SEQUENCE DESCRIPTION: SEQ ID NO:24:

TTAAGCTTGC ACCACGACCC C                                             21
```

DENGUE NUCLEIC ACID VACCINES THAT INDUCE NEUTRALIZING ANTIBODIES

CROSS REFERENCE TO RELATED PATENTS AND APPLICATIONS

This application is related to the Provisional Application for Patent entitled Dengue Nucleic Acid Vaccines That Induce Neutralizing Antibodies filed Jun. 4, 1996 by the inventors Tadeusz Kochel, Kevin R. Porter, Stephen L. Hoffman and Curtis G. Hayes, and Ser. No. 60/017,839, and is entitled to the benefit of the Jun. 4, 1996 filing date for the matter disclosed therein. That Provisional Application for Patent is incorporated herein by reference.

FIELD OF THE INVENTION

This invention relates to nucleic acid vaccines and more specifically to Dengue nucleic acid vaccines.

BACKGROUND OF THE INVENTION

Dengue (Den) viruses belong to the flavivirus genus of the family Flaviviridae and are of four serotypes, Den 1-4. Dengue viruses are positive strand RNA viruses which code for ten genes. The genes are translated as a polyprotein which is cleaved by host and viral proteinases. The virus envelope (E) protein is the major antigen against which neutralizing antibodies are directed. These antibodies have been shown to be capable of protecting against dengue virus infection[1]. The membrane protein also appears on the virion surface and is required for the proper processing of E.

Dengue viruses are transmitted primarily by the mosquito, *Aedes aegypti*, and are a major cause of morbidity and mortality throughout tropical and subtropical regions worldwide[2]. It is estimated that there are over 100 million cases, annually, of dengue fever[3]. Human dengue illnesses range from an acute undifferentiated fever to dengue hemorrhagic fever (DHF) and dengue shock syndrome (DSS). A primary infection usually causes dengue fever. The illness is generally mild and the person apparently acquires a life long immunity against the serotype of dengue virus causing the infection. However, if a person acquires a second dengue infection with a different serotype, the illness may be more severe and lead to hemorrhagic fever or shock syndrome, with a mortality rate between one and five percent. The increased severity of the secondary infection is caused by an immune enhancement phenomenon[4]. Immune enhancement begins when non-neutralizing antibodies, generated from the earlier infection with one dengue serotype, bind to but do not neutralize the virus causing the secondary infection. The Fc portion of the antibody in the virus-antibody complexes then binds to the Fc receptors present on mononuclear phagocytes of the immune system, resulting in enhanced infection of these cells. The enhanced infection leads to the release of cytokines that ultimately cause capillary leak and coagulopathy, the principal pathogenic mechanisms in DHF/DSS.

At present there is no approved vaccine for dengue viruses. The most effective dengue vaccine would elicit sustained protective levels of neutralizing antibodies against all four serotypes so as to avoid the possibility of immune enhancement in a vaccinated individual who might become secondarily infected with a different epidemic or endemic dengue of a different serotype.

Work in mice and primates with inactivated whole virus and at recombinant protein dengue vaccines has generally been disappointing because of the lack of sustained protective neutralizing antibodies induced. Vaccination with live attenuated dengue virus vaccines is another promising approach, but difficulties still remain in developing a product that is immunogenic and does not cause dengue fever-like side effects. DNA vaccines for dengue will offer substantial advantages over these other approaches in that sustained immunity can be achieved without the risk of dengue fever-like side effects or immune-enhancement.

A description of DNA inoculation was presented by Vical, Inc. (San Diego, Calif.)[5]. Vical demonstrated that one could inject a gene, (in the proper context of an eukaryotic expression vector), into the muscle of an animal and that the injected gene would be expressed. The expression vector must contain the proper eukaryotic transcriptional regulatory elements (promoter/enhancer and polyadenylation site) and a multiple cloning site so that once inside the cell of the subject the gene will be expressed. Once the gene is transcribed it is translated and processed to its mature protein product.

The basic DNA injection system offers great potential for vaccine development. One clones the genes which contain the desired antigenic determinates into an expression construct and injects the DNA into an animal. Since the proteins are translated and processed within the host cells, proper conformation of B cell epitopes on secreted proteins and induction of class 1 MHC-dependent immune responses should occur appropriately.

The technique of DNA injection is being used to develop vaccines against many pathogens including: Influenza[6], HIV[7], Hepatitis C[8], Malaria[9] and Herpes[10].

SUMMARY OF THE INVENTION

It is an object of this invention to protect a subject or community against infection by dengue virus.

It is another object of this invention to provide protection against infection by dengue virus by using a nucleic acid vaccine.

It is an object of this invention to provide protection against more than one dengue virus serotype.

These and additional objects of the invention are accomplished by taking the envelope (E) and optionally, the membrane (PreM) genes of dengue virus, serotypes 1, 2, 3, and 4 and cloning them into eukaryotic plasmid expression vectors. The resultant plasmid DNAs (dengue DNA vaccines) are injected into a mammalian subject where in vivo the E proteins are expressed and subsequently recognized and processed by immune cells. This results in the generation of humoral and cellular immunity that is protective against dengue virus infections of each of the four serotypes.

We have used the DNA injection technology to develop DNA vaccines against the Den viruses. We have cloned genes from each of the four Den serotype viruses into expression vectors and have assessed their potential as Den virus vaccines. The Den genes which we have incorporated into our DNA vaccines include: 80–100% of the E gene; either alone or expressed with the PreM gene. The choice of these genes systems from publications which demonstrate that: E contains the virus' major antigenic determinants[11]; not all of E is required to obtain a protective immune response[12]; and PreM affects the conformation of the produced E protein[13]. As Den virus DNA vaccines, some combinations of the above-listed genes yield better immune responses than others.

These and other objects, features and advantages of the present invention are described in or are apparent from the following detailed description of preferred embodiments.

BRIEF DESCRIPTION OF THE DRAWINGS

The invention will be described with reference to the drawings, in which like elements have been denoted throughout by like reference numerals. The representations in each of the figures is diagrammatic and no attempt is made to indicate actual scales or precise ratios. Proportional relationships are shown as approximations.

FIG. 5 is a Kaplan Meier Survival plot summarizing the results of a mouse challenge experiment using the dengue type 2 DNA vaccine.

FIG. 6 is a graph showing the immunogenicity of a Den 1 DNA vaccine containing 80% E.

FIG. 7 is a graph illustrating the immunogenicity of DNA vaccines constructed against dengue serotype 1 and containing the PreM gene and different amounts of the E gene.

FIG. 8 is a graph illustrating the immunogenicity of DNA vaccines constructed against dengue serotype 2 and against dengue serotype 3.

DETAILED DESCRIPTION OF THE INVENTION

By this invention the newly developed nucleic acid vaccination approach is adapted to provide a dengue virus vaccine, also called a naked DNA dengue vaccine. Eukaryotic plasmid expression vectors containing the PreM and at least part of the E gene of a virus selected from the group consisting of dengue-1 virus, dengue-2 virus, dengue-3 virus and dengue-4 virus are formed. The constructs are then injected into a mammalian subject; either individually or in combinations including up to all four serotypes. Nucleic acid vaccines possess many of the advantages of live-attenuated vaccines without the concern of inducing clinical illness by the vaccine itself. Since the viral proteins are translated and processed within the host cells, proper conformation of epitopes on secreted proteins and induction of class I MHC-dependent immune responses occur appropriately, and induction of both humoral and cellular immunity are long lasting. The invention applies nucleic acid vaccine technology to develop a DNA plasmid construct that elicits anti-dengue neutralizing antibodies in a mouse model which leads to and is adaptable to later application to other mammals, including non-human and human primates.

In general, the naked DNA dengue vaccine of the present invention includes the dengue preM gene, and at least part of the dengue E gene, for dengue type 1, 2, 3 or 4, or some combination of types 1, 2, 3 and 4. The published sequences for the preM and E genes of dengue serotype 1, West Pacific strain, serotype 2, New Guinea C strain, serotype 3, H87 strain, and serotype 4, H81 strain, are referred to herein as sequence id. nos. 4, 1, 5 and 6, respectively. The vaccine preferably includes at least about 80% and most preferably, about 100%, about 92% or about 80% of the dengue E gene. Alternatively, the vaccine of the present invention preferably includes about 100%, about 92% or about 80% of the dengue E gene and need not include any of the preM gene. Silent base substitutions may be made to the above-described DNA without altering the effectiveness or scope of the present invention. The DNA dengue vaccine of the present invention does not include any nucleotides or sequences susceptible to expression in a mammalian cell other than as described above.

The expression vector used to produce the above vaccine is a eukaryotic expression vector including a promotor/enhancer, cloning site and termination sequence. The promoter/enhancer works with RNA polymerase to initiate transcription of mRNA and the cloning site is for insertion of the dengue genes of interest. The expression vector preferably also includes an intron, which is not expressed in the protein produced by the mammalian cell but speeds up expression of the genes of interest.

The vaccine of the present invention is preferably administered by intradermal or intramuscular injection but any other means of administration known to persons of ordinary skill in the art may also be used. The vaccine is a pharmaceutical composition suitable for injection into a subject. It includes the above-described plasmid in a suitable injectable pharmaceutical carrier that does not interact with the plasmid. Examples of suitable carriers for the vaccine of the present invention are phosphate buffered saline (PBS) and normal saline (150 mM sodium chloride).

Experimental Results

This invention shows that the nucleic acid vaccination technique can be used to raise a protective anti-dengue virus immune response in mice. In the first series of experiments, two different plasmid expression vectors, pkCMVintPolyli and pVR1012 were used. A detailed description of pkCMVintPolyli and pVR1012 is given below under "Examples". Briefly, pkCMVintPolyli (developed by Vical, Inc.) is an expression vector which contains the CMV enhancer and CMV intron A, a multiple cloning site, the SV40 poly A site (termination sequence) and the SV40 origin of replication. The vector pVR1012, developed by Vical, Inc. and referred to herein as p1012, is an expression vector which contains the CMV enhancer, the CMV intron A sequence, a multiple cloning site, and the Bovine Growth Hormone termination sequence. p1012 does not include the SV40 origin of replication. The Den-2 genes PreM and 92% E were cloned into pkCMVintPolyli and p1012 (see "Examples" below for cloning details); the resultant constructs are pD2ME and p1012D2ME, respectively. The latter construct is also referred to herein as p1012D2ME92, the sequence of which is listed as sequence id. no. 2.

To determine if pD2ME and p1012D2ME properly express the E gene in vitro, Immune Fluorescence Assays (IFA) and Radio-labeled Immune Precipitation Analysis (RIPA) were performed on transiently transfected cells. Details of IFA, RIPA and transfections are provided below under "Examples" and the results of these measurements are shown in Table I.

TABLE I

Figure 1:
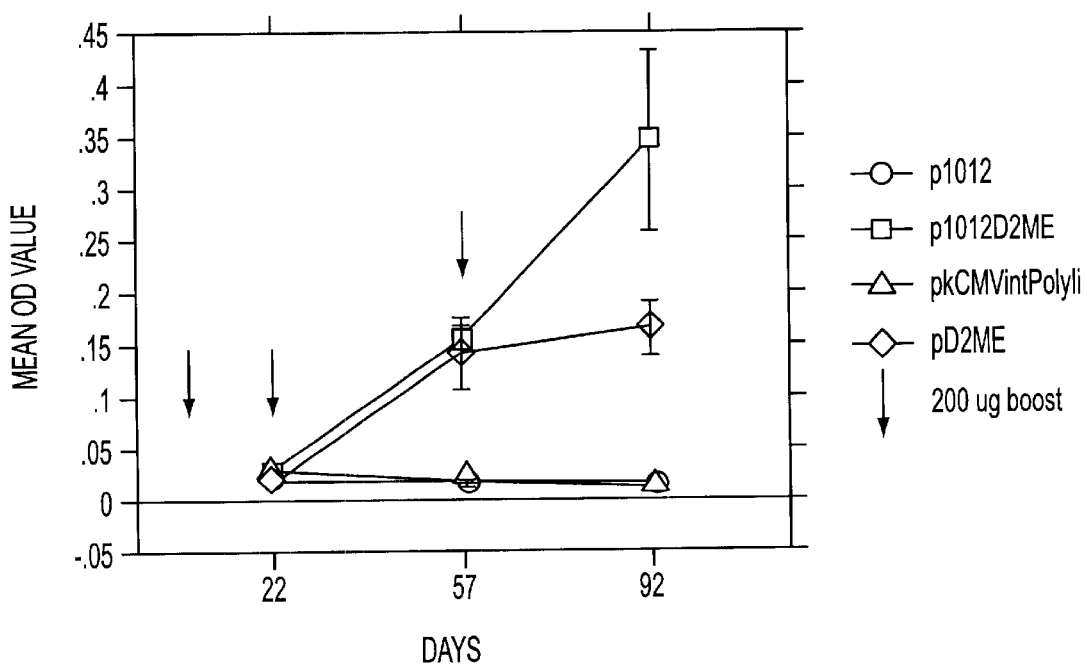
FIG. 1 is a graph showing time response to inoculation with two different Den type 2 DNA vaccines.

Immune Fluorescence Assay of Construct Transfected Cells

| Construct | Antisera | | |
|---|---|---|---|
| | Den-2 HIAF | 4G2 | 3H5 |
| pkCMVintPolyli | − | − | − |
| pVR1012 | − | − | − |
| PD2ME | ++ | ++ | ++ |
| p1012D2ME | +++ | +++ | +++ |

Adenovirus transformed human embryonic kidney cells (293 cells) were transfected with vector only (pkCMVintPolyli or pVR1012) or Den type-2 DNA vaccine (pD2ME or p1012D2ME). Forty eight hours post transfection the cells were scraped off their plates and spotted onto slides. The slides were then reacted with either Den-2 hyperimmune ascitic fluid (HIAF) or conformation specific anti-Den envelope antibodies 4G2 and 3H5. Fluorescein conjugated secondary antibody was used to visualize the primary antibody-antigen interaction by fluorescence. The slides were rated on a fluorescence scale of − (negative) to 4+ (four positive).

Table I shows that cells transfected with either pD2ME or p1012D2ME express the truncated E protein of Den-2. The ability of Den-2 Hyper-Immune Ascitic Fluid (HIAF) to recognize the truncated E protein in the IFA demonstrates the expression of the truncated E protein. No truncated E protein is expressed in cells transfected with vector only (i.e. pkCMVintPolyli or p1012). The proper expression of the truncated E gene, and retention of conformational epitopes, in vitro, is demonstrated by the ability of two, Den-2, conformation-dependent monoclonal antibodies, 4G2 and 3H5, to specifically recognize the protein.

Table I also shows that genes cloned into pVR1012 yield greater amounts of fluorescence than the same genes cloned into pkCMVintPolyli, thus suggesting that genes cloned into p1012 are expressed at higher levels than the same genes cloned into pkCMVintPolyli, in vitro. This observation was also seen in RIPA of identically transfected cells. Den-2 HIAF, 3H5 and 4G2 each immune precipitated greater amounts of the truncated E protein from cell lysates of p1012D2ME transfected cells than from pD2ME-transfected cells. RIPA also detected truncated E protein in the media of transfected cells demonstrating that the truncated E protein is secreted (data not shown).

To determine if pD2ME or p1012D2ME could induce the production of anti-Den antibodies in an in vivo system, mice were inoculated with the DNA constructs (detailed description of DNA inoculation and in vitro analysis of immune responses is presented below under "Examples"). Groups of ten three-week old mice were intradermally inoculated with either pVR1012, pkCMVintPolyli, pD2ME or p1012D2ME (on day 0) and boosted on days 9, 22 and 57 post priming. Sera were collected from the mice on days 22, 57 and 92 post priming (and day 154 for p1012D2ME inoculated mice) and assayed for the presence anti-Den antibodies by enzyme-linked immunosorbent assay (ELISA).

Referring now to FIG. 1 the time course of antibody production is shown. The three week old mice that were intradermally inoculated with pD2ME or p1012D2ME produced dengue antibodies, as manifested by ELISA results. Mice inoculated with pkCMVintPolyli or pVR10122 did not produce any Den antibodies. The mean ELISA optical density (OD) obtained from sera of mice inoculated with p1012D2ME was two-fold higher, after the third DNA boost, than that obtained from mice inoculated with pD2ME. It is believed that this phenomenon is due to the genes cloned into pVR1012 which shows a higher level of expression as compared with genes cloned into pkCMVintPolyli.

To determine if the Den-2 antibodies produced by pD2ME and p1012D2ME inoculated mice contain virus neutralizing activity, Plaque Reduction Neutralization Tests (PRNT) were performed, on day 92 (post priming) sera. The $PRNT_{50}$ for the sera from pD2ME and p1012D2ME inoculated mice are shown in Table II. Day 92 sera from mice inoculated with pkCMVintPolyli or p1012 did not produce Den-2 antibodies (See FIG. 1), nor did day 92 sera from those mice contain any Den-2 virus neutralizing activity (data not shown). All sera from mice inoculated with either pD2ME or p1012D2ME contain virus neutralizing activity. The mean reciprocal dilution titer for sera from mice immunized with pD2ME is 48. The mean reciprocal dilution titer for sera from p1012D2ME immunized mice is 195. The $PRNT_{50}$ titers for sera from p1012D2ME vaccinated mice are four times higher than those obtained from sera of pD2ME vaccinated mice. This result is not unexpected since the p1012D2ME vaccinated mice produced higher levels of Den-2 antibodies (as manifested by ELISA, See FIG. 1). The neutralizing titers obtained from both sets of mice are comparable to those titers previously shown in the literature to be sufficient to protect a mouse from a lethal challenge of Den virus. Mice immunized with Den virus produce $PRNT_{50}$ reciprocal titers as high as 360[14] and other Den virus vaccines have been shown to be protective against lethal challenge with titers as low as ten[15]. Thus, sera from the p1012D2ME vaccinated mice are producing $PRNT_{50}$ titers approaching that of Den virus.

TABLE II

Neutralizing antibody titers in mice immunized with p1012D2ME or pD2ME.

| p1012D2ME Sera | | pD2ME Sera | |
|---|---|---|---|
| Animal # | $PRNT_{50}$ | Animal # | $PRNT_{50}$ |
| 1 | 1:320 | 1 | 1:40 |
| 2 | 1:80 | 2 | 1:40 |
| 3 | 1:160 | 3 | 1:20 |
| 4 | 1:80 | 4 | 1:80 |
| 5 | 1:320 | 5 | 1:40 |
| 6 | 1:320 | 6 | 1:80 |
| 7 | 1:10 | 7 | 1:80 |
| 8 | 1:20 | 8 | 1:40 |
| 9 | 1:320 | 9 | 1:20 |
| 10 | 1:320 | 10 | 1:40 |

Figure 2:
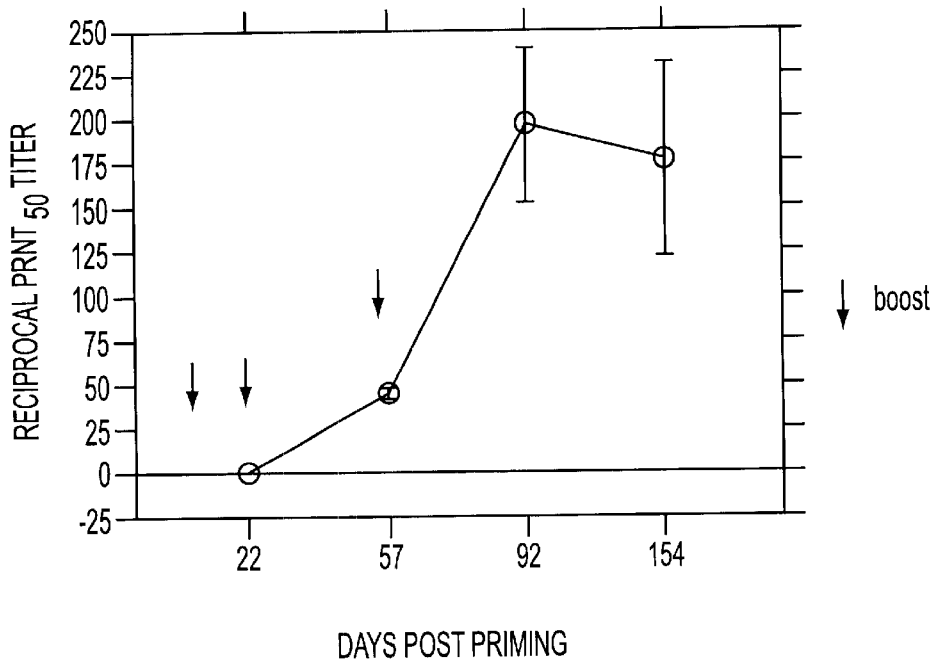
FIG. 2 is a graph showing the time course of plaque reduction neutralization test titers from sera of mice inoculated with p1012D2ME against Den type 2.

A desirable feature of a Den virus vaccine is that it be capable of affording sustained protection. The indicator of protection that we are using is $PRNT_{50}$ titers. The day 92 sera from p1012D2ME vaccinated mice contained mean reciprocal $PRNT_{50}$ titers of 195. Sera were collected from those same mice on day 154 (post priming) and assayed by ELISA for the presence of Den-2 antibodies and for neutralizing titers by $PRNT_{50}$. FIG. 2 shows that the mice were still producing high levels of Den-2 antibodies. The mean reciprocal $PRNT_{50}$ titers were still 190, demonstrating the sustained protective efficacy of our Den-2 DNA vaccine.

Neutralizing antibodies are an indicator of the protective efficacy of a vaccine, but direct protection from a lethal challenge of virus unequivocally demonstrates the efficacy of the vaccine. In the murine system, the standard dengue virus challenge is conducted with six week old mice since older mice are less susceptible to the virus[16]. Three week old mice are immunized and challenged three weeks later.

Ten mice were inoculated with p1012D2ME and challenged at six weeks of age (day 21 post priming), but protection was not observed. That result was not completely unexpected since in our system the mice did not produce significant amounts of Den antibodies at the time of challenge but did produce significant amounts of Den antibodies later (See, FIG. 1).

In light of the above results, an earlier antibody response would be desirable. Therefore, the use of immunostimulatory DNA sequences (ISS) and the effects of lower dosages when using ISS were explored. Groups of 5 mice were immunized ID with either 200 μg, 50 μg, 12.5 μg or 3.1 μg of the dengue 2 DNA vaccine p1012D2ME92. Additional groups of mice were co-immunized with the same amounts of vaccine together with 100 μg of the commercially available pUC 19 plasmid (Life Technologies/Gibco). The rationale for using pUC 19 is that in studies where plasmids coding for the protein beta galactosidase were co-injected with pUC 19, both cellular and humoral immunity to this protein in mice were enhanced[17]. The plasmid pUC 19 was found to contain two copies of the ISS (—AACGTT—) located in the ampicillin resistance gene.

Figure 3:
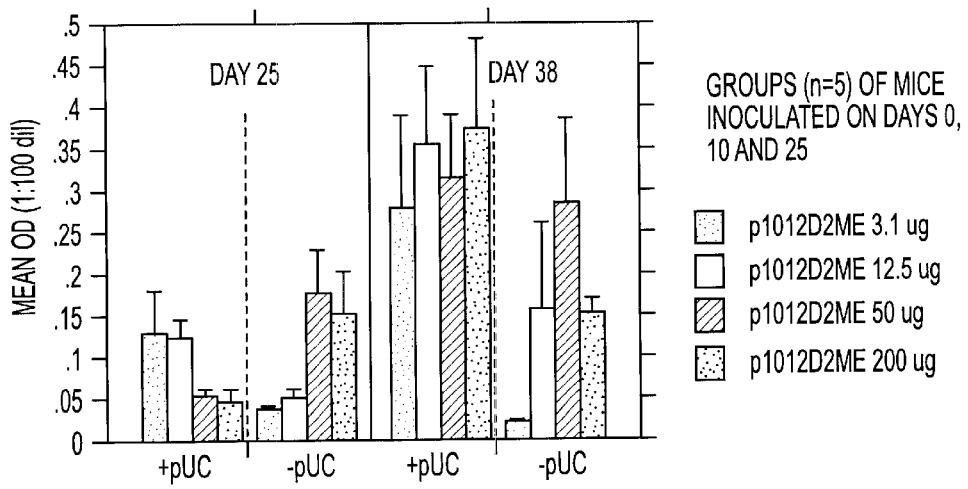
FIG. 3 is a bar graph showing the response to inoculation with various dosages of Den type 2 DNA vaccine +/− Immuno-stimulatory DNA sequences.

For these dosing studies, mice were primed on day 0 and boosted on days 10 and 25 and serum samples obtained on days 25 and 38. At day 25 (after a single boost) the dengue antibody response, as measured by mean OD value, in mice that received 3.1 μg and 12.5 μg of p1012D2ME was greater in the pUC group but the differences were not statistically significant. Referring now to FIG. 3, mice immunized with 50 μg and 200 μg of DNA vaccine without pUC had a significantly greater mean OD value compared to the mice that received the same dose along with pUC (FIG. 3). The detection of dengue antibody at day 25 in the 200 μg group contrasts earlier findings where dengue antibodies were not seen until approximately two months post-priming. The reason for this difference is not clear, but may be the result of improved inoculation techniques. By day 38, the mean OD values for the pUC group were higher throughout the range of doses compared to OD values for the group that received vaccine alone (FIG. 3).

However the only statistically significant difference was seen between the groups that were immunized with 3.1 μg (p<0.05), indicating that pUC significantly enhanced the immunogenicity of the dengue DNA vaccine at the lowest dosage.

Figure 4:
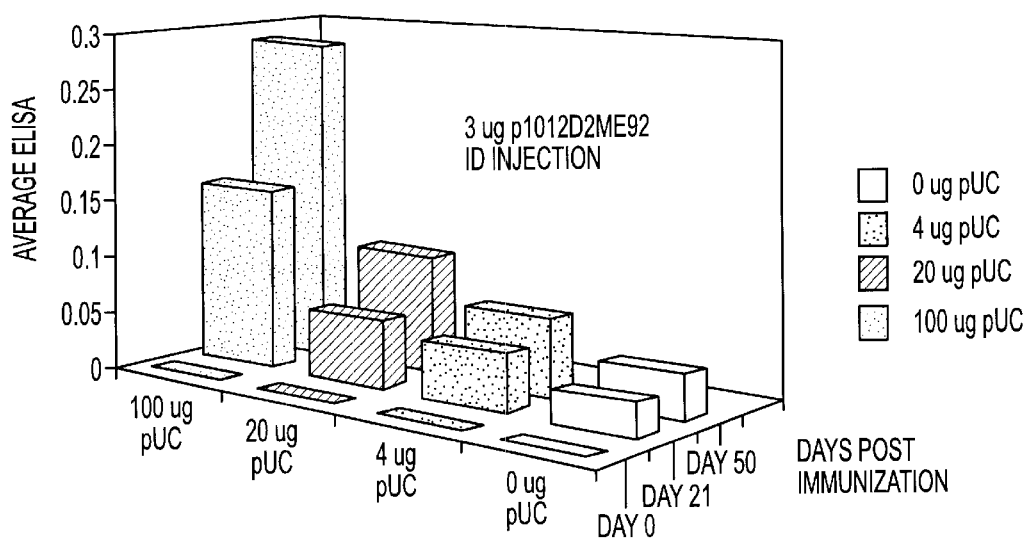
FIG. 4 is a bar graph showing the response to inoculation with suboptimal dose of p1012D2ME and various amounts of Immuno-stimulatory DNA sequences (puC).
Figure 5:
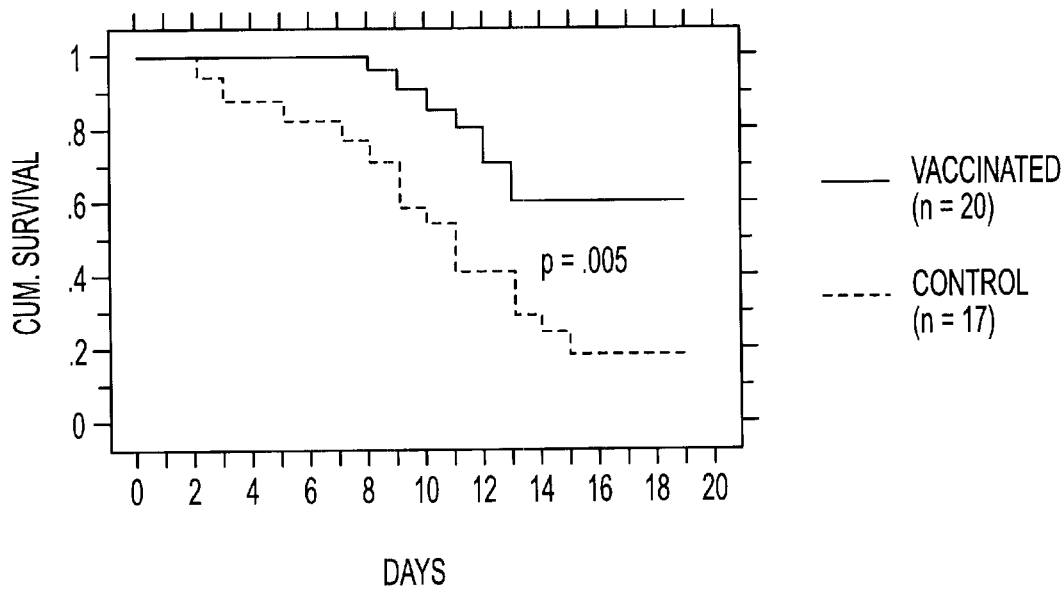
Figure 6:
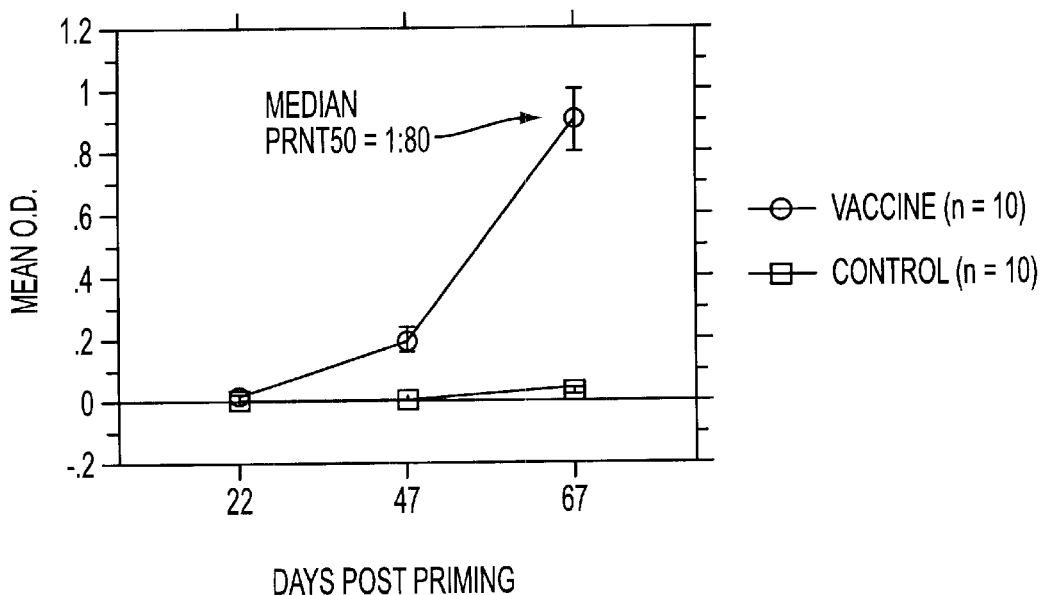

To further evaluate the immuno-stimulatory effects of pUC on the immune response to 3 μg of DNA vaccine, four groups of five mice each were co-immunized with 3 μg of p1012D2ME92 together with decreasing amounts of pUC (100 μg, 20 μg, 4 μg, and 0 μg). The mice were primed and then boosted on days 10 and 21. As shown in FIG. 4, serum samples obtained on day 21 (after the first boost) and on day 50 (after the second boost) showed a significantly greater antibody response, as measured by the mean ELISA OD, in the group of animals co-immunized with 100 μg of pUC. A dose-related decrease in mean OD was observed with a minimal antibody response occurring in the group of animals immunized with 3 μg of vaccine alone. Further analysis of the day 57 serum samples using the plaque reduction neutralization test showed that the mean neutralizing antibody titer in the group co-immunized with 100 μg pUC (1:48) was significantly greater (p<0.008) than the mean titer of the 4 μg (1:24) and 20 μg (1:14) groups. No neutralizing antibodies were detected in the group immunized with vaccine alone. These results indicate that ISS contained in pUC significantly enhances the neutralizing antibody response of the dengue DNA vaccine and that 100 μg of pUC 19 produced the greatest immunostimulatory effect.

Figure 7:
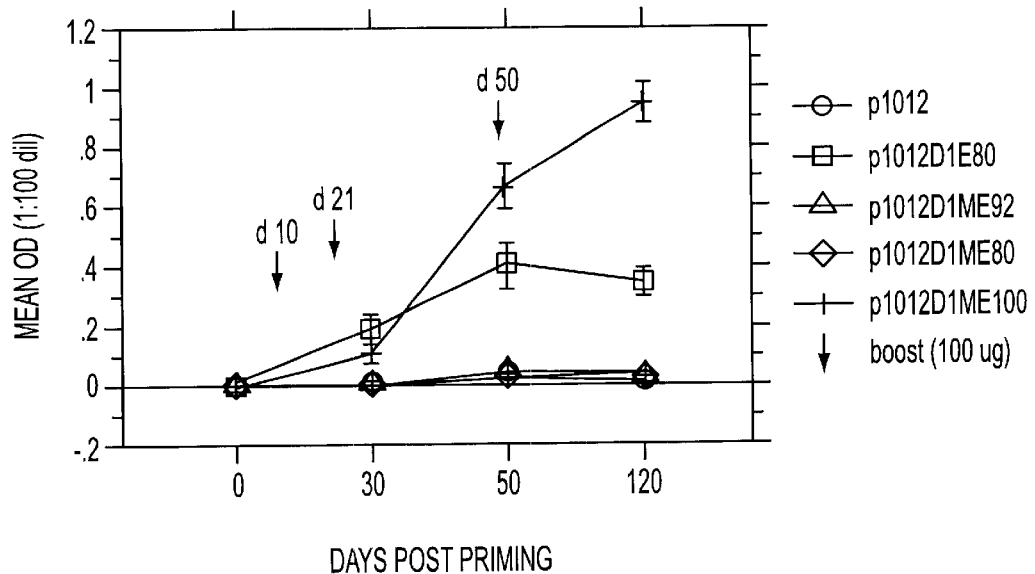

The protective efficacy in a mouse intracerebral challenge model using p1012D2ME92 with the co-inoculation of pUC 19 was evaluated. A more detailed description of the challenge can be found below under "Examples". Four groups of ten three-week old mice each were immunized with either 12.5 μg pVRO112 alone, 12.5 μg pVR1012 plus 100 μg pUC 19, 12.5 μg p1012D2ME92 plus 100 μg pUC 19 or 50 μg p1012D2ME92 alone. Mice were primed on day 0, boosted on day 10 post-priming and challenged on day 21 (when mice reached the appropriate challenge age of six weeks). Survival in the groups that received vaccine with or without pUC 19 was 60% compared to 20% and 10% in the pVR1012 only and pVR1012 plus pUC groups, respectively. Because of the small numbers in each group, only the comparison between the vaccine plus pUC 19 and the pVR1012 plus pUC groups showed a statistically significant difference in survival (Kaplan Meier analysis, $p<0.05$). However, as shown in FIG. 5, if the two vaccine groups and two control groups were combined, the difference in survival was more significant ($p=0.005$).

The above discussion describes Den 2 DNA vaccines. To demonstrate the feasibility of constructing a DNA vaccine against another serotype, 80% of the E gene of Den type 1 virus was cloned into the plasmid vector pkCMVintPolyli; the resultant plasmid is pD1E80 (details of cloning, in vitro, and in vivo experiments are described further below under "Examples"). Proper expression of 80% E off pD1E80, in vitro, was confirmed by IFA and RIPA. In vitro, 80% E was made in cells and secreted from the cells into the cell culture media (data not shown).

To determine if pD1E80 could induce an immune response in vivo, three week old mice were inoculated (on day 0) with either pD1E80 or pkCMVintPolyli and boosted on days 9, 21 and 47. Sera were collected from the mice on days 0, 22, 47 and 67 post priming and assayed for the presence of Den-1 antibodies by ELISA. The results are shown in FIG. 6. Mice injected with pkCMVintPolyli did not produce any Den-1 antibodies. Mice that were injected with pD1E80 produced Den-1 antibodies. The time course of antibody production was similar to that seen with the Den-2 DNA vaccines (See, FIG. 1). Day 67 sera were assayed for the presence of neutralizing activity by PRNT. The reciprocal $PRNT_{50}$ titers are shown in Table III. Sera from mice injected with pkCMVintPolyli contained no virus neutralizing activity. Sera from mice immunized with pD1E80 contained virus neutralizing activity. The mean reciprocal $PRNT_{50}$ titer is 80. Titers at this level should provide significant protection against lethal challenge.

TABLE III

Neutralizing Antibody Titers in Mice Immunized With pD1E80.

| Animal # | $PRNT_{50}$ |
|---|---|
| 1 | 1:40–1:80 |
| 2 | 1:40–1:80 |
| 3 | 1:40–1:80 |
| 4 | 1:80 |
| 5 | 1:40–1:80 |
| 6 | 1:40–1:80 |
| 7 | 1:160 |
| 8 | 1:40–1:80 |
| 9 | 1:40–1:80 |
| 10 | 1:80 |

The Den-1 80% E gene expressed from pkCMVintPolyli yielded a significant immune response in mice. Since in the dengue 2 experiments genes cloned into the other vector p1012 yielded greater antibody responses than the same genes cloned into pkMVintPolyli, Den 1 genes were cloned into p1012. To evaluate how much of the E gene to include to produce the optimum antibody response, DNA vaccine candidates p1012D1E80, p1012D1ME92, p1012D1ME80 and p1012D1ME100 were prepared. p1012D1E80 has 80% of Den 1 E cloned into p1012; p1012D1ME92 has the PreM and 92% of Den 1 E cloned into p1012; p1012D1ME80 has the PreM and 80% of Den 1 E cloned into p1012 and p1012D1ME100 has the PreM and 100% of Den 1 E cloned into p1012. All constructs were confirmed to express their E gene in vitro by IFA and RIPA (data not shown). To determine if the constructs could induce an immune response in vivo, three week old mice were inoculated (on day 0) with either p1012 or one of the DNA vaccine candidates and boosted on days 10 and 21. Sera were collected from the mice on days 0, 30 and 50 and assayed for the presence of Den-1 antibodies by ELISA. The results are shown in FIG. 7. Mice injected with p1012 did not produce Den-1 antibodies. Mice that were injected with p1012D1ME92 or p1012D1ME80 also did not produce any Den-I antibodies. Mice immunized with p1012D180 or p1012D1ME100 did produce Den 1 antibodies. The DNA vaccine candidate containing the PreM and 100% E elicited the best immune response.

Figure 8:
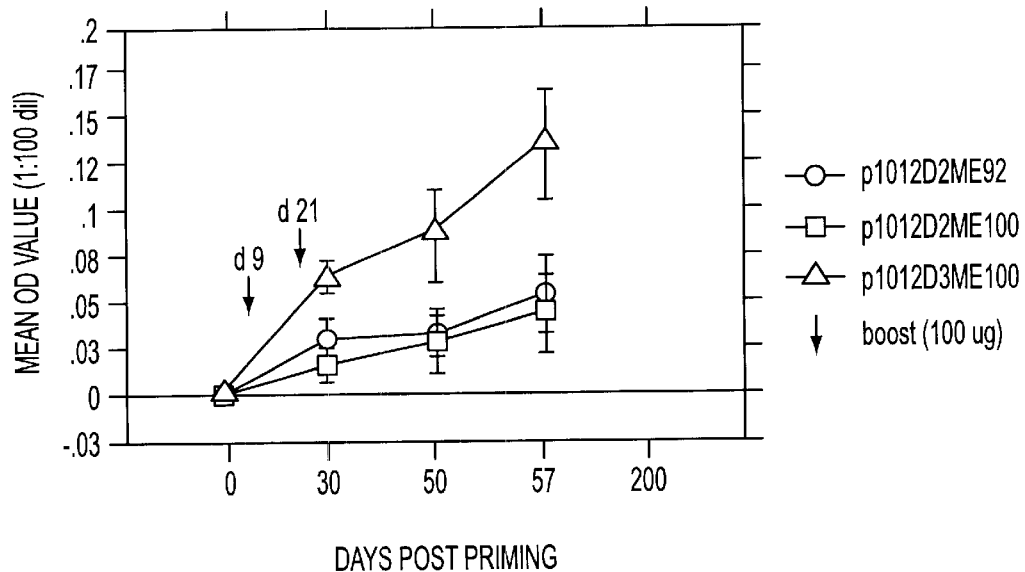

The results presented in this application demonstrate the ability of dengue DNA vaccines for dengue types 1 and 2 to elicit dengue antibody responses in mice. The dengue type 2 DNA vaccine was shown to provide significant protection against lethal dengue virus challenge. The neutralizing antibodies produced by the dengue DNA vaccine were shown to be long-lasting. Referring now to FIG. 8, similar DNA vaccine candidates that express the PreM and 100%E genes from Den virus serotype 2 and 3 produce dengue antibodies in mice as measured by ELISA. Mice have been inoculated with similar constructs for dengue 4 and it is expected that these constructs will have similar effects in producing dengue antibodies. A tetravalent dengue DNA vaccine that provides protection against all four serotypes can be prepared by combining the four different DNA vaccines to form a tetravalent mixture or, alternatively, by cloning various combinations of the genes into one or more plasmid vectors. Similarly, the combined vaccine can include 1, 2, 3 or 4 of the individual vaccines or the individual genes. It is expected that such a combined DNA vaccine would provide life-long protection against dengue virus infection without the risk of vaccine induced dengue fever-like side effects or the risk of making vaccinated persons vulnerable to the most severe clinical forms of the disease, DHF/DSS.

Having described the invention, the following examples are given to illustrate specific applications of the invention including the best mode now known to perform the invention.

EXAMPLE

Example 1

Preparation of Plasmid DNA Constructs

The plasmid vectors pkCMVintPolyli and pVR1012, used to construct the dengue DNA vaccines were kindly provided by Vical, Inc. PkCMVintPolyli is an expression vector which contains the CMV enhancer, CMV intron, a multiple cloning site, the SV40 poly A site and the SV40 origin of replication. pVR1012 (referred to as p1012) is an expression vector which contains the CMV enhancer, the intron A sequence, a multiple cloning site, and the Bovine Growth Hormone termination sequence. p1012 does not include the SV40 origin of replication. The dengue serotype 2 PreM/E genes were derived from a plasmid pkT2.4[18]. This plasmid contains the capsid (C), pre-membrane and envelope genes of dengue-2, New Guinea C strain. The dengue sequences spanning bases 1–2249 (including C, PreM and 92% of E) were retrieved from this plasmid by EcoR1 restriction enzyme digestion. The EcoR1 restriction fragment was polished with PFU polymerase (Statagene Cloning Systems, La Jolla, Calif.) and was then digested with Sal I restriction enzyme and cloned into the Sal I/EcoR V sites of pkCMVintPolyli. This resultant plasmid is called pCME. To remove C sequences, pCME was digested with Pst I, gel purified and re-ligated. The Pst I digestion removes sequences from the multiple cloning site to dengue-2 base 327. The resultant plasmid is called pD2ME and contains PreM and 92% E (bases 327–2249). pD2ME was sequenced on an ABI 377 automated DNA sequencer using Den-2 primers: P2, P4, P5 and P9 and pkCMVintPolyli primers TK1 and TK4. P2:5'-CATTGGATTTTGAACTGA, P4:5'-GTCACGATGGAGTGCTCT, P5:5'-GGATGTTGTTGTTTTGGGAT, P9:5'-CCTCTATACAGTACTTCCTTAGAGTGGC, TK1: 5'-GGTAACTCCCGTTGCGGTTCTG, TK4:5'-CATGGAAGCCATCACAGACGGC. The sequence analysis revealed that compared to the published Den-2 New Guinea C sequence[19], pD2ME contains two point mutations and sequences at the 3' end of E which code for seven non-Den-2 amino acids. The first point mutation is a G to A at base 532 and the second is a C to A at base 2221. The first mutation changes amino acid 68 of PreM from arginine to lysine and the second changes amino acid 454 of E from threonine to asparagine. Translation of pD2ME transcripts is expected to begin at codon 103 of Den-2 (base 330), which is the signal sequence for PreM, and proceed through amino acid 462 of E. Following amino acid 462 are the seven non-Den-2 amino acids (methionine, glutamic acid, leucine, serine, arginine, proline and leucine) and a termination codon.

To construct p1012D2ME, the Den-2 PreM/92% E fragment in pD2ME was removed by Pst I/Bgl II digestion and ligated into the multiple cloning site (Pst I/Bgl II sites) of the expression vector pVR1012.

The constructs p1012D1E80, p1012D1ME92, p1012D1ME80 and p1012D1ME100 were made by RT/PCR amplifying the Den-1 genes (West Pacific Strain) and cloning them into pVR1012. Den-1 virus RNA was purified from 0.5 ml of a crude virus stock by guanidine thiocyanate method. The RNA was reverse transcribed in a standard reaction using random hexamer primers (Phamacia) and RAV reverse transcriptase (Amersham Corporation). The resultant cDNA was used to amplify different segments of the virus genome using the following oligonucleotide primers (Life Technologies, Inc.):

```
a: 5'-ACG TCT CGA GAG GAC CAT GGC TGT GAC CAT GCT CCT CAT GCT
b: 5'-ACG TCT CGA GAG GAC CAT GGG GAT CAT TTT TAT TTT GCT GAT
c: 5'-ACG TGG ATC CTC ATT ACT TCT TGA ACC AGC TTA GTT TCA
```

-continued

```
d: 5'-AGT GGA TCC TCA TTA CTT CAT GGT CCA AGA AAC ACC
e: 5'-AGT GGA TCC TCA TTA CGC CTG AAC CAT GAC TCC TAG
```

| Genome Coordinates | Protein encoded | Primer pairs | Designation |
|---|---|---|---|
| 863–2089 | 80% E | b&c | E80 |
| 369–2089 | preM+80% E | a&c | ME80 |
| 369–2275 | preM+92% E | a&d | ME92 |
| 369–2392 | preM+100% E | a&e | ME100 |

The PCR products were purified by centrifugation through a Sephadex G 100 spin column followed by ethanol precipitation. The purified PCR products were digested with Xho I and Bam HI (sites provided in the PCR primers) and ligated into Sal I/Bam HI digested pVR1012 to get: p1012D1E80, p1012D1ME80, p1012D1ME92 and p1012D1ME100.

To make the Den-4 construct p1012D4ME100, the PreM and the entire E gene of Den-4 (Den-4 strain H421) was made by RT/PCR and cloned into pVR1012. Den-4 virus RNA was purified using a "Total Viral RNA Extraction Kit" (Qiagen, Inc.). The RNA was reverse transcribed in a standard reaction using the Den-4RT primer, 5'-TCC ACA CTT CAA TTC (Life Technologies, Inc.) and the reverse transcriptase enzyme Superscript (Life Technologies, Inc.). The Den-4RT primer hybridizes to Den-4 sequence coordinates 2468–2454. The PCR was performed using the reverse transcription product and Den-4 primers 1D4F and 7D4R (Life Technologies, Inc.). The sequence of 1D4F is: 5'-ATA CTG CAG GCA TGC TGA ACA TCC TGA ACG GGA GAA AAAG G. The Den-4 sequence coordinates of 1D4F are 367–398. The sequence of 7D4R is: 5'-TATGA TCC TTA TGC TTG AAC TGT GAA GCC CAG AAA CAG AGT G. The Den-4 sequence coordinates of 7D4R are 2420–2390. 1D4F contains a Pst I site and 7D4R contains a Bam HI site. The PCR product was digested with Pst I and Bam HI and ligated into the Pst I/Bam HI sites of pVR1012.

To make the Den-3 construct p1012D3ME100, the PreM and the entire E gene of Den-3 (Den-3 strain H87) was made by RT/PCR and cloned into pVR1012. Den-3 virus RNA was purified using a "Total Viral RNA Extraction Kit" (Qiagen, Inc.). The RNA was reverse transcribed in a standard reaction using the Den-3RT primer, 5'-GAC TAA AGG TAC GGT AT (Life Technologies, Inc.) and the reverse transcriptase enzyme Superscript (Life Technologies, Inc.). The Den-3RT primer hybridizes to Den-3 sequence coordinates 3420–3404. The PCR was conducted using the reverse transcription product and Den-3 primers 1D3F and D3R (Life Technologies, Inc.). The sequence of 1D3F is: 5'-AAA CTG CAG CCA TGC TGA GCA TTA TCA ACA AAC GGA AA. The Den-3 sequence coordinates of 1D3F are 364–391. The sequence of D3R is: 5'-TTA AGC TTG CAC CAC GAC CCC. The Den-3 sequence coordinates of D3R are 2413–2396. 1D3F contains a Pst I site; D3R does not contain a restriction site, the 5' end is blunt. The PCR product was digested with Pst I and ligated into the Pst I/Eco RV sites of pVR1012.

Example 2

Plasmid Preparation

Plasmids were transformed into *E. coli* DH5 cells, grown in the presence of kanamycin and purified by alkaline lysis[20]. Following alkaline lysis, the plasmids were double CsCl-Ethidium Bromide gradient purified, resuspended in PBS and stored at −20° C. until used.

Example 3

In vitro Analysis of Constructs

25% confluent 60 mm dishes of 293 cells were calcium phosphate transfected[21] with 15 μg Den DNA vaccine or 15 μg vector DNA. The cells were maintained in Dulbecco's Minimal Essential Media (DMEM) with 10% fetal calf serum and Penicillin/Streptomycin at 37° C. in 5% $CO_2$. The media was changed 12 hours post transfection. Thirty-six hours post transfection, the cells were washed with PBS and labeled with 50 μCi $^{35}$S-methionine (1000 Ci/mmole, ICN, Inc.) in 2 ml methionine deficient media for 12 hours. The media and the cells were then subject to immunoprecipitation with dengue-specific antisera. Prior to immunoprecipitation the media was removed and the cells were scraped off the plates and lysed in 1 ml RIPA buffer (0.05 M Tris-HCl (pH 7.5), 0.15 M NaCl, 1% NP-40, 0.5% Deoxycholate, 0.1% Sodium Dodecyl Sulfate (SDS). For the immunoprecipitations, media or 300 μl cell lysate was mixed with 5 μl antisera and 25 μl protein G sepharose (Life Technologies, Inc.) and incubated at 4° C. for 1 hour. The precipitates were then collected, washed twice with PBS, resuspended in Laemmli buffer (0.015 M Tris-HCl (pH 6.8) 0.1 M DTT, 2% SDS, 0.1% Bromophenol Blue, 10% glycerol), boiled for 10 minutes followed by 10% SDS-PAGE[22]. The gel was then fixed with 10% acetic acid, 25% methanol at 25° C. for 1 hour, treated with Amplify (Amersham, Inc.) for 30 minutes, dried and an autoradiogram was obtained.

For Immune Fluorescence Assays (IFA), cells were transfected as above. Forty-eight hours post transfection the media was removed from the cells, 1 ml PBS was added and the cells were scraped off the plates. The cells were washed twice with PBS and resuspended in 1 ml PBS. Ten μl aliquots were spotted onto slides, air dried and fixed with acetone. Ten μl primary sera, diluted 1:100 with PBS, was spotted onto cells and incubated at 37° C. for 1 hour. The slides were then washed twice with PBS. Ten μl secondary antisera (fluorescein conjugated goat IgG fraction to mouse immunoglobulin (Cappel, Inc.) diluted 1:100 in PBS and 0.05% Evans Blue was added to the cells. The cells were then incubated at 37° C. for one hour, washed twice with PBS, air dried and viewed using a Nikon microscope equipped with epifluorescence. The fluorescence was then rated from–(no fluorescence) to ++++ (maximum fluorescence).

Example 4

ELISA Detection of Den Antibodies in Mice Immunized with the Den DNA Vaccine Detection of mouse Den antibody: Sera were assayed for Den antibodies by enzyme-linked immunosorbent assay (ELISA). Den-1,2,3 or 4 (the appropriate virus for which the antiserum is being screened for) infected and uninfected Vero cell culture lysates were coated onto 96-well microtiter plates. The serum samples were diluted 1:25 or 1:100 in serum dilution buffer (5% skim milk and 0.1% Tween-20 in PBS), and added in duplicate to the Den antigen coated and uninfected antigen coated plates. After 1 hour incubation at 37° C, the plates were washed with PBS. Following the wash, horse radish peroxidase conjugated goat anti-mouse IgG, IgM and IgA (Kirkegaard and Perry Laboratories, Gaithersburg, Md.) was added to each well to detect bound mouse Den antibody. The wells were washed and a chromogenic substrate (ABTS: 2,2' Azino di 3-ethyl benzpyrazoline sulfonate) was added and allowed to incubate for 30 minutes at 37° C. Plates were then read at 410 nm. Adjusted OD values were calculated by subtracting the OD of the control antigen-coated well from the corresponding viral antigen-coated well. The cutoff OD value for determining antibody positivity was calculated as the mean adjusted OD of the negative control sera plus 3 standard deviations.

Example 5

Mice and DNA Injections

Groups of three week old Balb/c mice (Jackson Labs, Bar Harbor, Me.) were inoculated intradermally with plasmid DNA in a total volume of 50 µl of PBS. The amounts of Den DNA vaccine injected were as follows: pD2ME—200 µg; or p1012D2ME—200 µg, 50 µg, 12.5 µg and 3.1 µg; p1012D1E80, p1012D1ME92, p1012D1ME80 and p1012D1ME100—100 µg. The injections were given in the tail, approximately 2 cm from the base as previously described[23]. The mice were primed on day 0 and boosted on days 9, 21 and 57. Before the boosting, blood samples were obtained by the periorbital route. Blood samples were obtained approximately two weeks after the last boost were analyzed for dengue-specific antibodies using ELISA[24] and the plaque reduction neutralization test[25]. Sera from these samples were stored at −70° C. until used. Following injection mice were placed in segregated cages according to inoculation group and maintained in American Association for Laboratory Animal Care-approved quarters under pathogen-free conditions.

Example 6

Den-2 Virus challenge of Mice

Groups of twenty mice immunized with the DNA plasmids were challenged with Den-2 virus as described previously[26]. Briefly, three week old Balb/c mice were primed intradermally with either 12.5 µg p1012D2ME plus 100 µg pUC 19, 12.5 µg p1012, 50 µg p1012D2ME or 50 µg p1012 and boosted with the same DNAs and doses 9 days later. At six weeks of age the mice were challenged. Challenge virus was prepared from a Den-2 (New Guinea C) infected suckling mouse brain. Mice received 100 mouse 50% lethal doses of Den-2 intracranially. The mice were then monitored for signs of encephalitis and death.

Example 7

Use of the dengue DNA vaccines to immunize humans.

In animals DNA vaccines against dengue have been shown to elicit neutralizing antibodies that result in significant protection against lethal live-virus challenge. Human immunization, given either IM or ID, with dengue DNA vaccines should provide protection against infection by all four dengue serotypes.

The foregoing descriptions of the preferred embodiments are intended to be illustrative and not limiting. It will be appreciated that numerous modifications and variations can be made without departing from the spirit or scope of the present invention.

References

1. Heinz, F. X. & Roehrig, J. T. Immunochemistry of Viruses Vol. 2 The basis for Serodiagnosis and Vaccines (eds. van Regen Mortel, M. H. V. & Neurgth, A. R.) 289–305 (Elsevier Science (Biomedical Division), Amsterdam, 1990).
2. Halstead, S. B., 1984. Selective primary health care: Strategies for control of disease in the developing world. XI. Dengue. Rev. Infect. Dis., 6:251–264.
3. Halstead, S. B., Pathogenesis of Dengue: Challenges to Molecular Biology. Science 1988;239:476–481.
4. Kinks, S., Antibody-enhanced Infection of Monocytes as the Pathogenic Mechanism for Severe Dengue Illness. Aides Research and Human Retroviruses 1990; 6:993–998.
5. Wolf, J. A., Malone, R. W., Williams, P., Chong, W., Ascadi, G., Jani, A. & Felgner, P. L. Direct Gene Transfer into Mouse Muscle in Vivo. (1990) Science 247, 1465–1468.
6. Ulmer, J. B., Donnelly, J. J., Parker, S. E., Rhodes, G. H., Felgner, P. 1., Dwarki, V. J., Gromkowski, S. H., Deck, R. R., DeWitt, C. M., Friuedman, A., Hawe, L. A., Leander, K. R., Martinez, D., Perry, H. C., Shiver, J. W., Montgomery, D. L., Liu, M. A. Heterologous Protection Against Influenza by Injection of DNA Encoding a Viral Protein. Science 259, 1745–1749.
7. Wang, B., Ugen, K. E., Srikantan, V., Agadjanyan, M. J., Dang, K., Refaeli, Y., Sato, A. I., Boyer, J., Williams, W. V., Weiner, D. B. Gene Inoculation Generates Immune Responses Against Human Immunodeficiency Virus Type 1. Proc. Natl. Acad. Sci. USA Vol. 90, pp. 4156–4160.
8. Major, M. E., Vitvitski, L., Mink, M. A., Schleef, M., Whalen, R. G., Trepo, C., Inchauspe, G. DNA-Based Immunization with Chimeric Vectors for the Induction of Immune Responses against the Hepatitis C Virus Nucleocapsid. Journal of Virology, Sept. 1995, p. 5798–5805.
9. Sedegah, M., Hedstrom, R., Hobart, P., Hoffman, S. Protection Against Malaria by Immunization with Plasmid DNA Encoding Circumsporozoite Protein. Proc. Natl. Acad. Sci. USA Vol. 91, pp. 9866–9870.
10. Cox, G. J., Zamb, T. J., Babiuk, L. A. Bovine Herpesvirus 1: Immune Responses in Mice and Cattle Injected with Plasmid DNA. Journal of Virology, Sept. 1993, p. 5664–5667.
11. Schlesinger, W. 1977. Dengue Viruses. Virol Monogr 16:1 132.
12. Men, R., Bray, M., Lai, C. J. Carboxy-terminally Truncated Dengue Virus Envelope Glycoproteins Expressed on the Cell Surface and Secreted Extracellularly Exhibit Increased Immunogenicity in Mice. J. Virol. 65:1400–1407.
13. Konishi, E., Mason, P. W. Proper Maturation of the Japanese Encephalitis Virus Envelope Glycoprotein Requires Cosynthesis with the Premembrane Protein. Journal of Virology, Mar. 1993, p. 1672–1675.
14. Delenda, C., Frenkiel, M., Deubel, V. Protective Efficacy in Mice of a Secreted form of Recombinant Dengue-2 Virus Envelope Protein Produced in Baculovirus Infected Insect Cells. Arch. Virol. 1994, 139.197–207.

15. Men, R. et al., J. Virol. 65:1400–1407, supra note 12.
16. Cole, G. A., Charles, J., Wisseman, L. Pathogenesis of Type 1 Dengue Virus Infection in Suckling, Weaning and Adult Mice. Am. J. Epidemiol. 1969, 89,669–680.
17. Sato, Y. et al., Immunostimulatory DNA sequences necessary for effective intradermal gene immunization, Science, 1996, 273:352–4.
18. This plasmid was provided by Dr. R. Putnak, Walter Reed Army Institute of Research, Washington, DC and its sequence is listed in Irie, K., Mohan, P. M., Sasaguri, Y., Putnak, R., Padmanabhan, R., Sequence analysis of cloned dengue virus type 2 genome (New Guinea-C strain), Gene &5(2): 197–211 (Feb 20, 1989).
19. Gruenberg, A., Woo, W. S., Biedrzycka, A., Wright, P. J. Partial Nucleotide Sequence and Deduced Amino Acid Sequence of the Structural Proteins of Dengue Virus Type 2, New Guinea C and PUO-218 Strains. J. Gen. Virol. 1988, 69, 1391–1398.
20. Sambrook, J., Fritsch, E., Manniatis, T. Molecular Cloning a Laboratory Manual. Cold Spring Harbor Laboratory Press, Cold Spring Harbor, N.Y., 1989.
21. Sambrook, J., supra note 20.
22. Laemmli, E. K., 1970, Cleavage of structural proteins during the assembly of the head of bacteriophage T4, Nature 227:680–685.
23. Raz, E., Carson, D., Parker, S., Parr, T., Abai, A., Aichinger, G., Gromkowski, S., Singh, M., Lew, D., Yankauckas, M., Baird, S., Rhodes, G. Intradermal Gene Immunization: The Possible Role of DNA Uptake in the Induction of Cellular Immunity to Viruses. Proc. Natl. Acad. Sci. USA Vol. 91, pp. 9519–9523.
24. Ansari, M., Shope, R., Malik, S. Evaluation of vero cell lysate antigen for the ELISA of flaviviruses. J. Clin. Lab. 1993, Anal. 7: 230–237.
25. Eckels, K., Harrison, V., McCown, J., Russel, P. Isolation of Temperature Sensitive Dengue 2 Virus Under Conditions Suitable for Vaccine Development. Infect. Immun. 1976, 14, 1221–1227.
26. Cole, et al., Am. J. Epidemiol. 1969, 89,669–680, supra note 16.

What is claimed is:

1. A pharmaceutical composition capable of inducing an immune response in a mammalian subject, comprising an immunogenic amount of a eukaryotic plasmid expression vector in pharmaceutically acceptable form, wherein said plasmid expression vector is functional in mammalian subjects and includes preM and at least 92% of the envelope gene of a dengue W virus, where W is a number selected from the group consisting of 1, 2, 3 and 4.

2. The pharmaceutical composition of claim 1 further comprising a second plasmid including the PreM and at least 92% of the envelope gene of dengue X virus, where X is a number different from W and is selected from a the group consisting of 1, 2, 3 and 4.

3. The pharmaceutical composition of claim 2 further comprising a third plasmid including the PreM and at least 92% of the envelope gene of dengue Y virus, where Y is a number different from W and from X and is selected from the group consisting of 1, 2, 3 and 4.

4. The pharmaceutical composition of claim 3 further comprising a fourth plasmid including the PreM and at least 92% of the envelope gene of dengue Z virus, where Z is a number different from W, from X, and from Y, and is selected from the group consisting of 1, 2, 3 and 4.

5. The pharmaceutical composition of claim 1, further comprising a suitable pharmaceutical carrier.

6. The pharmaceutical composition of claim 5, which is in injectable form.

7. The pharmaceutical composition of claim 1, which is a vaccine capable of inducing a protective immune response in said mammalian subject, comprising an immunoprotective amount of said plasmid expression vector.

8. The vaccine of claim 7, which comprises a suitable pharmaceutical carrier, and is in injectable form.

9. A method of inducing an immune response in a mammalian subject, comprising the step of injecting the composition of claim 6.

10. A method of inducing a protective immune response in a mammalian subjects comprising the step of injecting the vaccine of claim 8.

11. The pharmaceutical composition of claim 2, further comprising a suitable pharmaceutical carrier.

12. The pharmaceutical composition of claim 11, which is in injectable form.

13. The pharmaceutical composition of claim 2, which is a vaccine capable of inducing a protective immune response in said mammalian subject, comprising an immunoprotective amount of said plasmid expression vector.

14. The vaccine of claim 13, which comprises a suitable pharmaceutical carrier, and is in injectable form.

15. A method of inducing an immune response in a mammalian subject, comprising the step of injecting the composition of claim 12.

16. A method of inducing a protective immune response in a mammalian subject comprising the step of injecting the vaccine of claim 14.

17. The pharmaceutical composition of claim 3, further comprising a suitable pharmaceutical carrier.

18. The pharmaceutical composition of claim 17, which is in injectable form.

19. The pharmaceutical composition of claim 3, which is a vaccine capable of inducing a protective immune response in said mammalian subject, comprising an immunoprotective amount of said plasmid expression vector.

20. The vaccine of claim 19, which comprises a suitable pharmaceutical carrier, and is in injectable form.

21. A method of inducing an immune response in a mammalian subject, comprising the step of injecting the composition of claim 18.

22. A method of inducing a protective immune response in a mammalian subject, comprising the step of injecting the vaccine of claim 20.

23. The pharmaceutical composition of claim 4, further comprising a suitable pharmaceutical carrier.

24. The pharmaceutical composition of claim 23, which is in injectable form.

25. The pharmaceutical composition of claim 4, which is a vaccine capable of inducing a protective immune response in said mammalian subject, comprising an immunoprotective amount of said plasmid expression vector.

26. The vaccine of claim 25, which comprises a suitable pharmaceutical carrier, and is in injectable form.

27. A method of inducing an immune response in a mammalian subject, comprising the step of injecting the composition of claim 24.

28. A method of inducing a protective immune response in a mammalian subject, comprising the step of injecting the vaccine of claim 26.

* * * * *